(12) United States Patent
Gans et al.

(10) Patent No.: US 10,053,396 B2
(45) Date of Patent: Aug. 21, 2018

(54) PROCESS FOR THE SPECIFIC ISOTOPIC LABELING OF METHYL GROUPS OF VAL, LEU AND ILE

(71) Applicants: COMMISSARIAT A L'ENERGIE ATOMIQUE ET AUX ENERGIES ALTERNATIVES, Paris (FR); CENTRE NATIONAL DE LA RECHERCHE SCIENTIFIQUE (CNRS), Paris (FR); UNIVERSITE JOSEPH FOURIER, Grenoble (FR)

(72) Inventors: Pierre Gans, Voreppe (FR); Jerome Boisbouvier, Grenoble (FR); Isabel Ayala, Pont de Claix (FR); Olivier Hamelin, Champagnier (FR)

(73) Assignees: COMMISSARIAT A L'ENERGIE ATOMIQUE ET AUX ENERGIES ALTERNATIVES, Paris (FR); CENTRE NATIONAL DE LA RECHERCHE SCIENTIFIQUE, Paris (FR); UNIVERSITE JOSEPH FOURIER, Grenoble (FR)

(*) Notice: Subject to any disclaimer, the term of this patent is extended or adjusted under 35 U.S.C. 154(b) by 0 days.

(21) Appl. No.: 15/620,850

(22) Filed: Jun. 13, 2017

(65) Prior Publication Data

US 2017/0275216 A1 Sep. 28, 2017

Related U.S. Application Data

(62) Division of application No. 13/520,882, filed as application No. PCT/IB2010/000282 on Jan. 6, 2010, now Pat. No. 9,708,228.

(51) Int. Cl.
| | |
|---|---|
| *C07B 59/00* | (2006.01) |
| *G01N 24/08* | (2006.01) |
| *C12P 21/02* | (2006.01) |
| *C07C 59/215* | (2006.01) |

(52) U.S. Cl.
CPC .......... *C07B 59/008* (2013.01); *C07B 59/001* (2013.01); *C07C 59/215* (2013.01); *C12P 21/02* (2013.01); *G01N 24/087* (2013.01); *G01N 2458/15* (2013.01)

(58) Field of Classification Search
None
See application file for complete search history.

(56) References Cited

U.S. PATENT DOCUMENTS 6,897,337 B2 * 5/2005 Fesik ................... C07C 59/347
562/575

FOREIGN PATENT DOCUMENTS

WO  00 61525  10/2000

OTHER PUBLICATIONS

Crout, D.H.G., et al., "The Base-catalysed Rearrangement of α-Acetolactate (2-Hydroxy-2-methyl-3-oxobutanoate): a Novel Carboxylate Ion Migration in a Tertiary Ketol Rearrangement," Journal of the Chemical Society, Perkins Transactions I, pp. 1982-1989, (Jan. 1, 1979).
Crout, D.H.G., et al., "Absolute Configuration of the Product of the Acetolactate Synthase Reaction by a Novel Method of Analysis using Acetolactate Decarboxylase," Journal of the Chemical Society, Perkins Transactions I, pp. 1367-1369, (Jan. 1, 1990).
International Search Report dated Sep. 16, 2010 in PCT/IB10/00282 Filed Jan. 6, 2010.
"Isotopic Enrichment", IUPAC. Compendium of Chemical Terminology, 2$^{nd}$ Ed. (the "Gold Book"). Compiled by A.D. McNaught and A. Wilkinson. Blackwell Scientific Publications, Oxford (1997).
"Compound". Dictionary.com Unabridged. Retrieved Aug. 30, 2016 from Dictionary.com website http://www.dictionary.com/browse/compound.

* cited by examiner

*Primary Examiner* — Christopher Adam Hixson
*Assistant Examiner* — Michelle Adams
(74) *Attorney, Agent, or Firm* — Oblon, McClelland, Maier & Neustadt, L.L.P.

(57) ABSTRACT

A process for the specific isotopic labeling of an amino acid selected from Valine (Val), Leucine (Leu), and Isoleucine (Ile), in proteins and biomolecular assemblies by introducing, in a medium containing bacteria overexpressing a protein, an acetolactate derivative of Formula I of the application.

12 Claims, No Drawings

PROCESS FOR THE SPECIFIC ISOTOPIC LABELING OF METHYL GROUPS OF VAL, LEU AND ILE

REFERENCE TO PRIOR APPLICATIONS

This application is a division of U.S. application Ser. No. 13/520,882, filed Jul. 24, 2012, now allowed; which is a 371 of PCT/IB2010/000282, filed Jan. 6, 2010, the disclosures of which are incorporated herein by reference in their entireties.

The invention relates to a process for the specific isotopic labeling of Valine, Leucine and Isoleucine amino acids and more particularly for the stereospecific labeling of methyl groups of Leucine and Valine as well as specific labeling of the γ2 methyl groups of Isoleucine in proteins and biomolecular assemblies.

It also relates to specifically methyl labeled 2-hydroxy-2-methyl-3-oxobutanoic acid and 2-ethyl-2-hydroxy-3-oxobutanoic acid (named as acetolactate derivatives in the following) used in this process and to a process for manufacturing such specifically methyl labeled acetolactate derivatives.

NMR spectroscopy is an established and powerful method for structural determination and to map biomolecular interactions in complexes with affinities ranging from low nanomolar range to a few millimolar range.

But poor resolution in NMR spectra remains a major limiting factor to the application of this method to large molecular assemblies such as proteins of molecular weight up to 1 megadalton, even though recent progress in NMR spectroscopy of high molecular weight proteins have been made. This progress is strongly connected to the development of new isotopic labeling schemes. The combination of selected protonation of methyl groups in fully perdeuterated proteins with transverse relaxation optimized methyl spectroscopy (methyl-TROSY) has allowed local structure and dynamic proteins assemblies of up to 1 megadalton to be studied by solution NMR spectroscopy.

Such labeling protocols rely on the addition of specific [$^1$H$^{13}$C] methyl labeled biosynthetic precursors as the sole proton source in a perdeuterated culture medium.

This approach provides a high level of methyl protonation without detectable isotopic scrambling.

Valine (Val) and Leucine (Leu) and Isoleucine (Ile) are amino acids of great interest as their methyl groups account for more than 50% of the total methyl probes available in proteins.

Protonation of Leu and Val methyl groups in perdeuterated proteins is commonly achieved using methyl protonated 2-oxo-3-methylbutanoic acid (named α-ketoisovalerate in the following) an intermediate in the biosynthesis of such amino acids.

However, in particular for large proteins of 30 kDa to 1 megaDa, this labeling strategy can result in overcrowded [$^1$H$^{13}$C]-correlation spectra due to the sheer number of NMR-visible methyl-probes. Overlap in NMR spectra can greatly complicate the measurement of site-specific structural or relaxion parameters.

The invention aims to overcome the drawbacks of this method by providing a process for specific isotopic labeling of Valine, Leucine and Isoleucine amino acids and more particularly for the labeling of methyl groups of Leucine, Valine and Isoleucine in recombinant perdeuterated proteins.

This process offers a significant enhancement in the resolution and sensitivity of [$^{13}$C$^1$H]-methyl TROSY spectra and extends the capacity for detecting long-range structurally meaningful distance restraints in large proteins. This method is particularly useful for investigation of molecular interactions within large biomolecular assemblies.

Furthermore this process allows for proteins of little and medium size (i.e. of less than 100 kDa) a significant improvement for the stereospecific assignment of methyl groups of the Leucine and Valine aminoacids compared to precedent methods using mixture of unlabeled and labeled precursors (glucose or pyruvate). This last method is described in D. Neri, T. Szyperski, G. Otting, H. Senn, K. Wüthrich, *Biochemistry* 1989, 28, 7510-7516.

For this end, the invention proposes a process for the specific isotopic labeling of amino acids selected from the group consisting of Val, Leu, and lie, and more particularly for the stereospecific labeling of methyl groups of Leu and Val as well as specific labeling of the γ2 methyl groups of Isoleucine in proteins and biomolecular assemblies comprising the following step a):

introducing, in a medium containing bacteria overexpressing a protein, a 2-alkyl-2-hydroxy-3-oxobutanoic acid, wherein the alkyl substituent in position 2 is ethyl or methyl, also called acetolactate derivatives in the following and having the following formula:

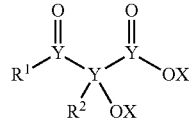

Formula I wherein:
X is $^1$H or $^2$H (D),
each Y is independently from the others $^{12}$C or $^{13}$C,
R$^1$ is a methyl group in which the carbon atom is $^{13}$C or $^{12}$C and the hydrogen atoms are independently from each other $^1$H or $^2$H (D),
R$^2$ is either a methyl group in which the carbon atom is $^{13}$C or $^{12}$C and the hydrogen atoms are independently from each other $^1$H or $^2$H (D), or an ethyl group in which the carbon atoms are independently from each other $^{13}$C or $^{12}$C and the hydrogen atoms are independently from each other $^1$H or $^2$H (D),
at the provisos that:
1) the hydrogen atoms of the acetolactate derivative of Formula I are not all, at the same time, either $^1$H or $^2$H (D),
2) the hydrogen atoms of R$^1$ and the hydrogen atoms of R$^2$ are not all, at the same time, either $^1$H or $^2$H (D).

In Formula I, X is an exchangeable hydrogen which can be $^1$H or $^2$H depending on the nature of the solvent.

This process furthermore comprises the following steps:
b) overexpression of the protein by the bacteria contained in the medium, and
c) purification of the protein.

In a first preferred embodiment of the process of labeling of the invention, the acetolactate derivative has the Formula I in which:
R$^1$ is chosen among the following groups:
$^{12}$CH$_3$, $^{12}$CD$_3$, $^{13}$CH$_3$, $^{13}$CD$_3$, $^{13}$CHD$_2$, $^{13}$CH$_2$D,
R$^2$ is chosen among the following groups:
$^{12}$CH$_3$, $^{12}$CD$_3$, $^{13}$CH$_3$, $^{13}$CD$_3$, $^{13}$CHD$_2$, $^{13}$CH$_2$D, $^{12}$CH$_3$$^{12}$CD$_2$, $^{12}$CD$_3$$^{12}$CD$_2$, $^{13}$CH$_3$$^{12}$CD$_2$, $^{13}$CH$_3$$^{13}$CD$_2$, $^{13}$CD$_3$$^{13}$CD$_2$, $^{13}$CHD$_2$$^{13}$CD$_2$, $^{13}$CH$_2$D$^{13}$CD$_2$, $^{13}$CHD$_2$$^{12}$CD$_2$, $^{13}$CH$_2$D$^{12}$CD$_2$,
each Y is independently from the others $^{12}$C or $^{13}$C,
at the provisos that:
1) the hydrogen atoms of the acetolactate derivative of Formula I are not all, at the same time, either $^1$H or $^2$H (D), 2) the hydrogen atoms of $R^1$ and the hydrogen atoms of $R^2$ are not all, at the same time, either $^1H$ or $^2H$ (D).

In a second preferred embodiment of the process of labeling of the invention, the acetolactate derivative is selected in the group of compounds having the following formulae:
4=2-hydroxy-2-($^{13}C$)methyl-3-oxo-4($^2H_3$)butanoic acid,
5=2-hydroxy-2-($^2H_3$)methyl-3-oxo-4($^{13}C$)butanoic acid,
6=2-($^2H_5$)ethyl-2-hydroxy-3-oxo-4-($^{13}C$)methylbutanoic acid,
9=1,2,3,4-($^{13}C$)-2-($^2H_5$)ethyl-2-hydroxy-3-oxobutanoic acid,
21=1,2,3-($^{13}C$)-2-($^{13}C$)methyl-2-hydroxy-3-oxo-4-($^2H_3$)butanoic Acid,
22=1,2,3,4-($^{13}C$)-2-($^2H_3$)methyl-2-hydroxy-3-oxobutanoic acid,
24=1,2,3-($^{13}C$)-2-(1'-($^2H_2$), $^{13}C_2$)ethyl)-2-hydroxy-3-oxo-4-($^2H_3$)butanoic acid,
36=3,4-($^{13}C$)-2-($^{13}C$)methyl-2-hydroxy-3-oxo-4-($^2H_3$)butanoic acid,
37=3,4-($^{13}C$)-2-($^2H_3$, $^{13}C$)methyl-2-hydroxy-3-oxobutanoic acid
40=3,4-($^{13}C$)-2-($^{13}C$)methyl-2-hydroxy-3-oxobutanoic acid,
45=3,4-($^{13}C$)-2-(1'-($^2H_2$), $^{13}C_2$)ethyl-2-hydroxy-3-oxo-4-($^2H_3$)butanoic acid,
46=3,4-($^{13}C$)-2-($^2H_5$, $^{13}C_2$)ethyl-2-hydroxy-3-oxobutanoic acid,
49=3,4-($^{13}C$)-2-(1'-($^2H_2$), $^{13}C_2$)ethyl-2-hydroxy-3-oxobutanoic acid.

In a third preferred embodiment of the process of labeling of the invention, the acetolactate derivative is selected in the group of compounds having the following formulae:
13=2-hydroxy-2-($^2H_2$, $^{13}C$)methyl-3-oxo-4-($^2H_3$)butanoic acid,
14=2-hydroxy-2-($^2H_3$)methyl-3-oxo-4-($^2H_2$, $^{13}C$)butanoic acid,
15=2-($^2H_5$)ethyl-2-hydroxy-3-oxo-4-($^2H_2$, $^{13}C$)butanoic acid,
34=2-(1'-($^2H_2$),2'-($^2H$),2'-($^{13}C$))ethyl-2-hydroxy-3-oxo-4-($^2H_3$)butanoic acid.

In a fourth preferred embodiment of the process of labeling of the invention, acetolactate derivative is selected in the group of compounds of the following formulae:
10=2-hydroxy-2-($^2H$, $^{13}C$)methyl-3-oxo-4-($^2H_3$)butanoic acid,
11=2-hydroxy-2-($^2H_3$)methyl-3-oxo-4-($^2H$, $^{13}C$)butanoic acid,
12=2-($^2H_5$)ethyl-2-hydroxy-3-oxo-4-($^2H$, $^{13}C$)butanoic acid.

The invention also proposes a compound of the following formula I-1:

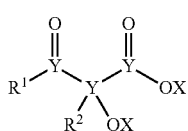

Formula I-1 wherein:
X is $^1H$ or $^2H$ (D),
each Y is independently from the others $^{12}C$ or $^{13}C$,
$R^1$ is a methyl group in which the carbon atom is $^{13}C$ or $^{12}C$ and the hydrogen atoms are independently from each other $^1H$ or $^2H$ (D), $R^2$ is either a methyl group in which the carbon atom is $^{13}C$ or $^{12}C$ and the hydrogen atoms are independently from each other $^1H$ or $^2H$ (D), or an ethyl group in which the carbon atoms are independently from each other $^{13}C$ or $^{12}C$ and the hydrogen atoms are independently from each other $^1H$ or $^2H$ (D),
at the provisos that:
1) the hydrogen atoms of the acetolactate derivative of Formula I are not all, at the same time, either $^1H$ or $^2H$ (D),
2) the hydrogen atoms of $R^1$ and the hydrogen atoms of $R^2$ are not all, at the same time, either $^1H$ or $^2H$ (D),
3) when all the hydrogen atoms of $R^1$ are $^2H$, then the carbon atoms, in formula I-1, are not all, at the same time, $^{12}C$.

The preferred compounds of the invention are selected from the group consisting of the compounds having the formula I-1 in which:
$R^1$ is chosen among the following groups:
$^{12}CH_3$, $^{12}CD_3$, $^{13}CH_3$, $^{13}CD_3$, $^{13}CHD_2$, $^{13}CH_2D$,
$R^2$ is chosen among the following groups:
$^{12}CH_3$, $^{12}CD_3$, $^{13}CH_3$, $^{13}CD_3$, $^{13}CHD_2$, $^{13}CH_2D$, $^{12}CH_3{}^{12}CD_2{}^{12}CD_3{}^{12}CD_2$, $^{13}CH_3{}^{12}CD_2$, $^{13}CH_3{}^{13}CD_2$, $^{13}CD_3{}^{13}CD_2$, $^{13}CHD_2{}^{13}CD_2{}^{13}CH_2D^{13}CD_2$, $^{13}CHD_2{}^{12}CD_2$, $^{13}CH_2D^{12}CD_2$,
each Y is independently from the others $^{12}C$ or $^{13}C$,
at the provisos that:
1) the hydrogen atoms of the acetolactate derivative of Formula I are not all, at the same time, either $^1H$ or $^2H$ (D),
2) the hydrogen atoms of $R^1$ and the hydrogen atoms of $R^2$ are not all, at the same time, either $^1H$ or $^2H$ (D), and
3) when all the hydrogen atoms of $R^1$ are $^2H$, then the carbon atoms, in formula I-1, are not all, at the same time, $^{12}C$.

It is to be noted that the active part of the acetolactate derivatives of formula I is, in fact the anion of the following formula:

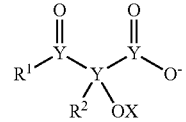

wherein:
X, Y, $R^1$ and $R^2$ are as defined for the compounds of formulae I and I-1.

In a first preferred embodiment, the compound of formula I-1 of the invention is selected among the compounds of the following formulae:
4=2-hydroxy-2-($^{13}C$)methyl-3-oxo-4($^2H_3$)butanoic acid,
5=2-hydroxy-2-($^2H_3$)methyl-3-oxo-4($^{13}C$)butanoic acid,
6=2-($^2H_5$)ethyl-2-hydroxy-3-oxo-4-($^{13}C$)methylbutanoic acid,
9=1,2,3,4-($^{13}C$)-2-(2H_5)ethyl-2-hydroxy-3-oxobutanic acid,
21=1,2,3-($^{13}C$)-2-($^{13}C$)methyl-2-hydroxy-3-oxo-4-($^2H_3$)butanoic Acid,
22=1,2,3,4-($^{13}C$)-2-($^2H_3$)methyl-2-hydroxy-3-oxobutanoic acid,
24=1,2,3-($^{13}C$)-2-(1'-($^2H_2$), $^{13}C_2$)ethyl)-2-hydroxy-3-oxo-4-($^2H_3$)butanoic acid,
36=3,4-($^{13}C$)-2-($^{13}C$)methyl-2-hydroxy-3-oxo-4-($^2H_3$)butanoic acid,
37=3,4-($^{13}C$)-2-($^2H_3$, $^{13}C$)methyl-2-hydroxy-3-oxobutanoic acid
40=3,4-($^{13}C$)-2-($^{13}C$)methyl-2-hydroxy-3-oxobutanoic acid, 45=3,4-($^{13}$C)-2-(1'-($^2$H$_2$),$^{13}$C$_2$)ethyl-2-hydroxy-3-oxo-4-($^2$H$_3$)butanoic acid,
46=3,4-($^{13}$C)-2-($^2$H$_5$, $^{13}$C$_2$)ethyl-2-hydroxy-3-oxobutanoic acid,
49=3,4-($^{13}$C)-2-(1'-($^2$H$_2$),$^{13}$C$_2$)ethyl-2-hydroxy-3-oxobutanoic acid.

In a second preferred embodiment, the compound of formula I-1 of the invention is selected among the compounds of the following formulae:
13=2-hydroxy-2-($^2$H$_2$, $^{13}$C)methyl-3-oxo-4-($^2$H$_3$)butanoic acid,
14=2-hydroxy-2-($^2$H$_3$)methyl-3-oxo-4-($^2$H$_2$, $^{13}$C)butanoic acid,
15=2-($^2$H$_5$)ethyl-2-hydroxy-3-oxo-4-($^2$H$_2$, $^{13}$C)butanoic acid,
34=2-(1'-($^2$H$_2$),2'-($^2$H),2'-($^{13}$C))ethyl-2-hydroxy-3-oxo-4-($^2$H$_3$)butanoic acid.

In a third preferred embodiment, the compound of formula I-1 of the invention is selected among the compounds of the following formulae:
10=2-hydroxy-2-($^2$H, $^{13}$C)methyl-3-oxo-4-($^2$H$_3$)butanoic acid,
11=2-hydroxy-2-($^2$H$_3$)methyl-3-oxo-4-($^2$H, $^{13}$C)butanoic acid,
12=2-($^2$H$_5$)ethyl-2-hydroxy-3-oxo-4-($^2$H, $^{13}$C)butanoic acid.

The invention also proposes a process for manufacturing a compound of the following formula I:

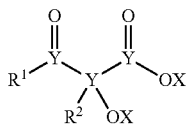

Formula I comprising the following steps:
a) alkylation with a methyl group in which the carbon atom is $^{13}$C or $^{12}$C and the hydrogen atoms are independently from each other $^1$H or $^2$H (D), or an ethyl group in which the carbon atoms are independently from each other $^{13}$C or $^{12}$C and the hydrogen atoms are independently from each other $^1$H or $^2$H (D), of a 3-oxobutanoate derivative having its hydroxyl group in position 1 protected by a protecting group, preferably a methyl or ethyl group,
b) hydroxylation of the compound obtained in step a),
c) optionally deprotection and exchange of the desired $^1$H atoms by $^2$H atoms,
wherein step b) of hydroxylation is carried out by using dimethyldioxirane in presence of Nickel (II) ions.

Furthermore, the invention also proposes processes for analysing proteins by NMR.

In a first embodiment, this process comprises a step of labeling the proteins to be analysed by the labeling process of the invention.

In a second embodiment, this process comprises a step of labeling the proteins to be analysed with a compound of the following formula I:

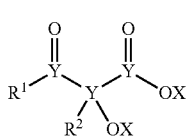

Formula I wherein:
X is $^1$H or $^2$H (D),
each Y is independently from the others $^{12}$C or $^{13}$C,
R$^1$ is a methyl group in which the carbon atom is $^{13}$C or $^{12}$C and the hydrogen atoms are independently from each other $^1$H or $^2$H (D),
R$^2$ is either a methyl group in which the carbon atom is $^{13}$C or $^{12}$C and the hydrogen atoms are independently from each other $^1$H or $^2$H (D), or an ethyl group in which the carbon atoms are independently from each other $^{13}$C or $^{12}$C and the hydrogen atoms are independently from each other $^1$H or $^2$H (D),
at the provisos that:
1) the hydrogen atoms of the acetolactate derivative of Formula I are not all, at the same time, either $^1$H or $^2$H (D),
2) the hydrogen atoms of R$^1$ and the hydrogen atoms of R$^2$ are not all, at the same time, either $^1$H or $^2$H (D).

In a third embodiment, this process comprises a step of labeling the proteins to be analysed with a compound of the following formula I-1:

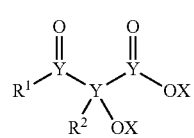

Formula I-1 wherein:
X is $^1$H or $^2$H (D),
each Y is independently from the others $^{12}$C or $^{13}$C,
R$^1$ is a methyl group in which the carbon atom is $^{13}$C or $^{12}$C and the hydrogen atoms are independently from each other $^1$H or $^2$H (D),
R$^2$ is either a methyl group in which the carbon atom is $^{13}$C or $^{12}$C and the hydrogen atoms are independently from each other $^1$H or $^2$H (D), or an ethyl group in which the carbon atoms are independently from each other $^{13}$C or $^{12}$C and the hydrogen atoms are independently from each other $^1$H or $^2$H (D),
at the provisos that:
1) the hydrogen atoms of the acetolactate derivative of Formula I are not all, at the same time, either $^1$H or $^2$H (D),
2) the hydrogen atoms of R$^1$ and the hydrogen atoms of R$^2$ are not all, at the same time, either $^1$H or $^2$H (D),
3) when all the hydrogen atoms of R$^1$ are $^2$H, then the carbon atoms, in formula I-1, are not all, at the same time, $^{12}$C.

The invention will be better understood and other features and advantages thereof will be more apparent when reading the following description.

In the description of the invention, the following terms have the following meanings:
Val designates amino acids Valine,
Leu designates amino acids Leucine,
Ile designates amino acids Isoleucine,
C designates $^{13}$C,
C designates $^{12}$C,
D designates $^2$H,
H designates $^1$H,
proR, proS: the methyl groups on the γ and β carbons of respectively unlabeled Leu and Val aminoacids, are not different and consequently the γ and β carbon of respectively unlabeled Leu and Val aminoacids are not chiral. But when the groups R$^1$ and R$^2$ are not labeled in the same manner in the acetolactate derivatives of formula I, the resulting methyl groups on the γ and β carbon of respectively Leu and Val are differently labeled and due to this difference the γ and β carbon of respectively Leu and Val become chiral. These methyl groups are designated as proR when labeling gives rise to a R configuration and as proS when labeling gives rise to a S configuration.

"Acetolactate derivative" designates compounds of formula I and their corresponding esters, preferably methyl esters or ethyl esters.

Biomolecular assemblies: molecules containing proteins and other groups.

The process of labeling of the invention is based on the use of acetolactate derivatives which have methyl or ethyl groups specifically labeled. These acetolactate derivatives are introduced in a medium containing bacteria overexpressing a protein or proteins of interest.

Otherwise stated, the process of the invention is based on the stereospecific rearrangement of labeled or unlabeled alkyl groups in acetolactate derivatives occurring in vivo in the early steps of Leu, Val and Ile biogenesis.

The proposed process of the invention for the specific isotopic labeling of methyl groups of amino acids, which are selected from the group consisting of Valine (Val), Leucine (Leu), and Isoleucine (Ile), in proteins comprises the following step a):

introducing, in a medium containing bacteria overexpressing a protein, a derivative of acetolactate having the following formula:

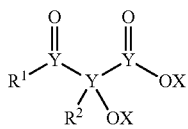

Formula I wherein:

X is an exchangeable hydrogen being $^1H$ or $^2H$ (D) depending on the nature of the solvent, i.e. X is $^1H$ when the solvent is $H_2O$ and X is $^2H$ when the solvent is $D_2O$, each Y is independently from the others $^{12}C$ or $^{13}C$, $R^1$ is a methyl group in which the carbon atom is $^{13}C$ or $^{12}C$ and the hydrogen atoms are independently from each other $^1H$ or $^2H$ (D), $R^2$ is either a methyl group in which the carbon atom is $^{13}C$ or $^{12}C$ and the hydrogen atoms are independently from each other $^1H$ or $^2H$ (D), or an ethyl group in which the carbon atoms are independently from each other $^{13}C$ or $^{12}C$ and the hydrogen atoms are independently from each other $^1H$ or $^2H$ (D), at the provisos that:

1) the hydrogen atoms of the acetolactate derivative of Formula I are not all, at the same time, either $^1H$ or $^2H$ (D), 2) the hydrogen atoms of $R^1$ and the hydrogen atoms of $R^2$ are not all, at the same time, either $^1H$ or $^2H$ (D).

Then, this process comprises a step of culture of the medium for overexpressing the protein(s) of interest and the purification and isolation of the protein(s).

Preferably, the acetolactate derivatives of formula I are selected in the group consisting of the compounds of the following formulae:

$R^1$ is chosen among the following groups:
$^{12}CH_3$, $^{12}CD_3$, $^{13}CH_3$, $^{13}CD_3$, $^{13}CHD_2$, $^{13}CH_2D$, $R^2$ is chosen among the following groups:
$^{12}CH_3$, $^{12}CD_3$, $^{13}CH_3$, $^{13}CD_3$, $^{13}CHD_2$, $^{13}CH_2D$, $^{12}CH_3^{12}CD_2$, $^{12}CD_3^{12}CD_2$, $^{13}CH_3^{12}CD_2$, $^{13}CH_3^{13}CD_2$, $^{13}CD_3^{13}CD_2$, $^{13}CHD_2^{13}CD_2$, $^{13}CH_2D^{13}CD_2$, $^{13}CHD_2^{12}CD_2$, $^{13}CH_2D^{12}CD_2$, each Y is independently from the others $^{12}C$ or $^{13}C$, at the provisos that:

1) the hydrogen atoms of the acetolactate derivative of Formula I are not all, at the same time, either $^1H$ or $^2H$ (D), 2) the hydrogen atoms of $R^1$ and the hydrogen atoms of $R^2$ are not all, at the same time, either $^1H$ or $^2H$ (D).

These acetolactate derivatives have the following formulae 1-57 in which:

($^{13}C$) methyl means that the carbon atoms of the methyl groups is $^{13}C$, ($^{13}C_2$) ethyl means that the two carbon atoms of the ethyl groups are $^{13}C$, $^2H_n$, in which n=1, 2, 3, 4 or 5 means that the n hydrogen atoms are $^2H$, and U means that all the carbon atoms are $^{13}C$:

1=2-hydroxy-2-methyl-3-oxo-4-($^2H_3$)butanoic acid,
2=2-hydroxy-2-($^2H_3$)methyl-3-oxobutanoic acid,
3=2-($^2H_5$)ethyl-2-hydroxy-3-oxobutanoic acid,
4=2-hydroxy-2-($^{13}C$)methyl-3-oxo-4-($^2H_3$)butanoic acid,
5=2-hydroxy-2-($^2H_3$)methyl-3-oxo-4-($^{13}C$)butanoic acid,
6=2-($^2H_5$)ethyl-2-hydroxy-3-oxo-4-($^{13}C$)methylbutanoic acid,
7=U—($^{13}C$)-2-hydroxy-2-methyl-3-oxo-4($^2H_3$)butanoic acid,
8=U—($^{13}C$)-2-hydroxy-2-($^2H_3$)methyl-3-oxobutanoic acid,
9=1,2,3,4-($^{13}C$)-2-($^2H_5$)ethyl-2-hydroxy-3-oxobutanoic acid,
10=2-hydroxy-2-($^2H$, $^{13}C$)methyl-3-oxo-4-($^2H_3$)butanoic acid,
11=2-hydroxy-2-($^2H_3$)methyl-3-oxo-4-($^2H$, $^{13}C$)butanoic acid,
12=2-($^2H_5$)ethyl-2-hydroxy-3-oxo-4-($^2H$, $^{13}C$)butanoic acid,
13=2-hydroxy-2-($^2H_2$, $^{13}C$)methyl-3-oxo-4-($^2H_3$)butanoic acid,
14=2-hydroxy-2-($^2H_3$)methyl-3-oxo-4-($^2H_2$, $^{13}C$)butanoic acid,
15=2-($^2H_5$)ethyl-2-hydroxy-3-oxo-4-($^2H_2$, $^{13}C$)butanoic acid,
16=U—($^{13}C$)-2-hydroxy-2-($^2H_2$)methyl-3-oxo-4-($^2H_3$)butanoic acid,
17=U—($^{13}C$)-2-hydroxy-2-($^2H_3$)methyl-3-oxo-4-($^2H_2$)butanoic acid,
18=1,2,3,4-($^{13}C$)-2-($^2H_5$)ethyl-2-hydroxy-3-oxo-4-($^2H_2$)butanoic acid,
19=2-(1'-($^2H_2$)ethyl-2-hydroxy-3-oxo-4-($^2H_3$)butanoic acid,
20=2-((1'-($^2H_2$),2'-($^{13}C$))ethyl-2-hydroxy-3-oxo-4-($^2H_3$)butanoic acid,
21=1,2,3-($^{13}C$)-2-($^{13}C$)methyl-2-hydroxy-3-oxo-4-($^2H_3$)butanoic acid,
22=1,2,3,4-($^{13}C$)-2-($^2H_3$)methyl-2-hydroxy-3-oxobutanoic acid,
23=U—($^{13}C$)-2-($^2H_5$)ethyl-2-hydroxy-3-oxobutanoic acid,
24=1,2,3-($^{13}C$)-2-(1'-($^2H_2$), $^{13}C_2$)ethyl)-2-hydroxy-3-oxo-4-($^2H_3$)butanoic acid,
25=U—($^{13}C$)-2-(1'-($^2H_2$))ethyl-2-hydroxy-3-oxo-4-($^2H_3$) butanoic acid,
26=U—($^{13}C$)-2-($^2H$)methyl-2-hydroxy-3-oxo-4-($^2H_3$)butanoic acid, 27=U—($^{13}$C)-2-($^2$H$_3$)methyl-2-hydroxy-3-oxo-4-($^2$H)butanoic acid,
28=U—($^{13}$C)-2-(($^2$H$_5$)ethyl)-2-hydroxy-3-oxo-4-($^2$H)butanoic acid,
29=1,2,3-($^{13}$C)-2-($^2$H, $^{13}$C)methyl-2-hydroxy-3-oxo-4-($^2$H$_3$)butanoic acid,
30=1,2,3,4-($^{13}$C)-2-($^2$H$_3$)methyl-2-hydroxy-3-oxo-4-($^2$H)butanoic acid,
31=1,2,3,4-($^{13}$C)-2-($^2$H$_5$)ethyl-2-hydroxy-3-oxo-4-($^2$H)butanoic acid,
32=U—($^{13}$C)-2-(1'-($^2$H$_2$),2'-($^2$H))ethyl-2-hydroxy-3-oxo-4-($^2$H$_3$)butanoic acid,
33=1,2,3-($^{13}$C)-2-(2'-($^2$H),$^{13}$C$_2$)ethyl-2-hydroxy-3-oxo-4-($^2$H$_3$)butanoic acid,
34=2-(1'-($^2$H$_2$),2'-($^2$H),2'-($^{13}$C))ethyl-2-hydroxy-3-oxo-4-($^2$H$_3$)butanoic acid,
35=1,2,3-($^{13}$C)-2-($^2$H$_2$, $^{13}$C)methyl-2-hydroxy-3-oxo-4-($^2$H$_3$)butanoic acid,
36=3,4-($^{13}$C)-2-($^{13}$C)methyl-2-hydroxy-3-oxo-4-($^2$H$_3$)butanoic acid,
37=3,4-($^{13}$C)-2-($^2$H$_3$, $^{13}$C)methyl-2-hydroxy-3-oxobutanoic acid,
38=3,4-($^{13}$C)-2-($^2$H$_2$, $^{13}$C)methyl-2-hydroxy-3-oxo-4-($^2$H$_3$)butanoic acid,
39=3,4-($^{13}$C)-2-($^2$H, $^{13}$C)methyl-2-hydroxy-3-oxo-4-($^2$H$_3$)butanoic acid,
40=3,4-($^{13}$C)-2-($^{13}$C)methyl-2-hydroxy-3-oxobutanoic acid,
41=3,4-($^{13}$C)-2-($^2$H, $^{13}$C)methyl-2-hydroxy-3-oxo-4-($^2$H)butanoic acid,
42=3,4-($^{13}$C)-2-($^2$H$_2$, $^{13}$C)methyl-2-hydroxy-3-oxo-4-($^2$H$_2$)butanoic acid,
43=3,4-($^{13}$C)-2-($^2$H$_3$, $^{13}$C)methyl-2-hydroxy-3-oxo-4-($^2$H$_2$)butanoic acid,
44=3,4-($^{13}$C)-2-($^2$H$_3$, $^{13}$C)methyl-2-hydroxy-3-oxo-4-($^2$H)butanoic acid,
45=3,4-($^{13}$C)-2-(1'-($^2$H$_2$), $^{13}$C$_2$)ethyl-2-hydroxy-3-oxo-4-($^2$H$_3$)butanoic acid,
46=3,4-($^{17}$C)-2-($^2$H$_5$, $^{13}$C$_2$)ethyl-2-hydroxy-3-oxobutanoic acid,
47=3,4-($^{13}$C)-2-(1'-($^2$H$_2$),2'-($^2$H)$^{13}$C$_2$)ethyl-2-hydroxy-3-oxo-4-($^2$H$_3$)butanoic acid,
48=3,4-($^{13}$C)-2-(1'-($^2$H$_2$),2'-($^2$H$_2$),$^{13}$C$_2$)ethyl-2-hydroxy-3-oxo-4-($^2$H$_3$)butanoic acid,
49=3,4-($^{13}$C)-2-(1'-($^2$H$_2$),$^{13}$C$_2$)ethyl-2-hydroxy-3-oxobutanoic acid,
50=3,4-($^{13}$C)-2-(1'-($^2$H$_2$),2'-($^2$H$_2$),$^{13}$C$_2$)ethyl-2-hydroxy-3-oxo-4-($^2$H$_2$)butanoic acid,
51=3,4-($^{13}$C)-2-(1'-($^2$H$_2$)-2'-($^2$H),$^{13}$C$_2$)ethyl-2-hydroxy-3-oxo-4-($^2$H)butanoic acid,
52=3,4-($^{13}$C)-2-(2H$_5$, $^{13}$C$_2$)ethyl-2-hydroxy-3-oxo-4-($^2$H$_2$)butanoic acid,
53=3,4-($^{13}$C)-2-(2H$_5$, $^{13}$C$_2$)ethyl-2-hydroxy-3-oxo-4-($^2$H)butanoic acid,
54=U—($^{13}$C)-2-($^2$H$_5$)ethyl-2-hydroxy-3-oxo-4-($^2$H$_2$)butanoic acid,
55=U—($^{13}$C)-2-($^2$H$_5$)ethyl-2-hydroxy-3-oxo-4-($^2$H)butanoic acid,
56=1,2,3-($^{13}$C)-2-(1'-($^2$H$_2$),2'-($^2$H$_2$),$^{13}$C$_2$)ethyl-2-hydroxy-3-oxo-4-($^2$H$_3$)butanoic acid,
57=U—($^{13}$C)-2-(1'-($^2$H$_2$),2'-($^2$H$_2$))ethyl-2-hydroxy-3-oxo-4-($^2$H$_3$)butanoic acid.

In order to better illustrate the formulae of the compounds of the invention, the developed formulae of compounds 1-18 are given below.

In these formulae, X designates $^2$H or $^1$H, D designates $^2$H, C designates $^{13}$C and C designates $^{12}$C:

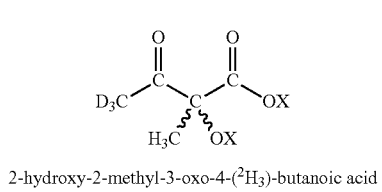

2-hydroxy-2-methyl-3-oxo-4-($^2$H$_3$)-butanoic acid

Formula 1

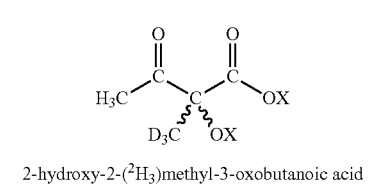

2-hydroxy-2-($^2$H$_3$)methyl-3-oxobutanoic acid

Formula 2

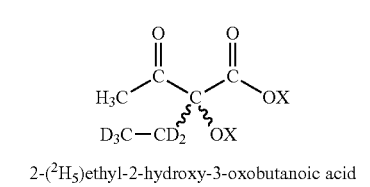

2-($^2$H$_5$)ethyl-2-hydroxy-3-oxobutanoic acid

Formula 3

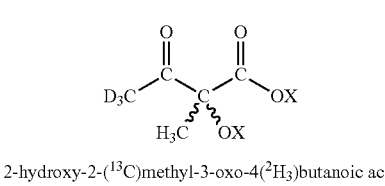

2-hydroxy-2-($^{13}$C)methyl-3-oxo-4($^2$H$_3$)butanoic acid

Formula 4

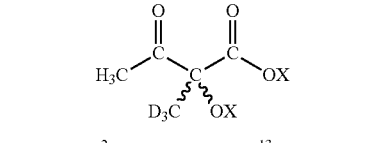

2-hydroxy-2-($^2$H$_3$)methyl-3-oxo-4($^{13}$C)butanoic acid

Formula 5

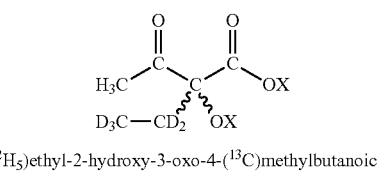

2-($^2$H$_5$)ethyl-2-hydroxy-3-oxo-4-($^{13}$C)methylbutanoic acid

Formula 6

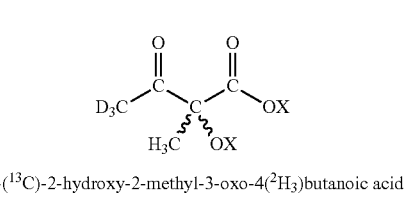

U-($^{13}$C)-2-hydroxy-2-methyl-3-oxo-4($^2$H$_3$)butanoic acid

Formula 7

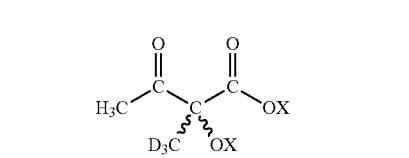

U-($^{13}$C)-2-hydroxy-2-($^2$H$_3$)methyl-3-oxobutanoic acid

Formula 8

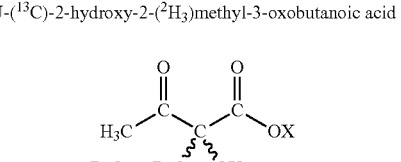

1,2,3,4-($^{13}$C)-2-($^2$H$_5$)ethyl-2-hydroxy-3-oxobutanoic acid

Formula 9

Formula 10

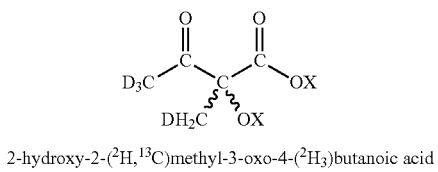

2-hydroxy-2-($^2$H,$^{13}$C)methyl-3-oxo-4-($^2$H$_3$)butanoic acid

Formula 11

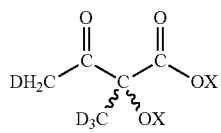

2-hydroxy-2-($^2$H$_3$)methyl-3-oxo-4-($^2$H,$^{13}$C)butanoic acid

Formula 12

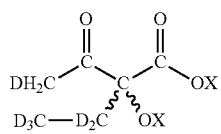

2-($^2$H$_5$)ethyl-2-hydroxy-3-oxo-4-($^2$H,$^{13}$C)butanoic acid

Formula 13

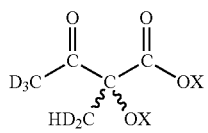

2-hydroxy-2-($^2$H$_2$,$^{13}$C)methyl-3-oxo-4-($^2$H$_3$)butanoic acid

Formula 14

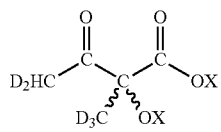

2-hydroxy-2-($^2$H$_3$)methyl-3-oxo-4-($^2$H$_2$,$^{13}$C)butanoic acid

Formula 15

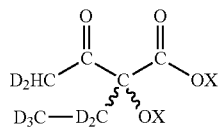

2-($^2$H$_5$)ethyl-2-hydroxy-3-oxo-4-($^2$H$_2$,$^{13}$C)butanoic acid

Formula 16

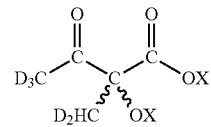

U-($^{13}$C)-2-hydroxy-2-($^2$H$_2$)methyl-3-oxo-4-($^2$H$_3$)butanoic acid

Formula 17

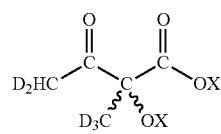

U-($^{13}$C)-2-hydroxy-2-($^2$H$_3$)methyl-3-oxo-4-($^2$H$_2$)butanoic acid

Formula 18

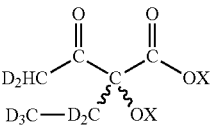

1,2,3,4-($^{13}$C)-2-($^2$H$_5$)ethyl-2-hydroxy-3-oxo-4-($^2$H$_2$)butanoic acid More specifically, when the compound of formula 1 is used in the process of the invention, the protonated methyl groups are proS methyl groups of Valine (γ2 methyl) and proS methyl groups of Leucine (δ2 methyl) and are $^{12}$CH$_3$.

Thus this compound enables to perform structural studies of proteins containing Leu and Val amino acids. The labeling with this compound enables to determine the stereospecificity of the amino acids Val and Leu and also enables to detect weak as low as 0.05 Hz, dipolar and scalar interactions in proteins of less than 30 kDa.

This compound of formula 1 (2-hydroxy-2-methyl-3-oxo-4-($^2$H$_3$)-butanoic acid) enables to label amino acids Leu and Val incorporated in proteins in the following manner:

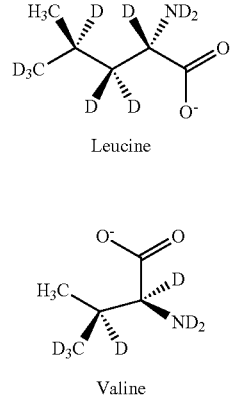

When this compound of formula 1 is used to produce human ubiquitine and protein G of *streptoccocus* (GB3) using *E. coli* cells in a deuterated M9 medium using 300 mg/l of this compound of formula 1, only the proS methyl groups of Val and Leu are protonated in these proteins and are then observable in the NMR 1D spectra of the obtained compounds.

The compound of formula 2 (2-hydroxy-2-($^2$H$_3$)methyl-3-oxobutanoic acid) enables to stereospecifically label with $^{12}$CH$_3$ proR methyl groups of Leu and Val. This compound enables to perform structural studies, stereospecific attribution and detection of weak dipolar and scalar interactions by NMR in proteins of less than 30 kDa.

The stereospecific labeling of these methyl groups with compound 2 gives the following labeling of amino acids Leu and Val:

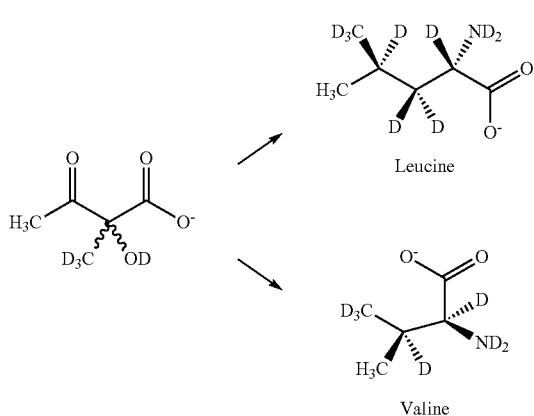

In NMR 1D spectra of proteins obtained by culture of a medium containing this compound of formula 2, only proR methyl groups of Leucine and Valine, more precisely the γ1 methyl group of Valine and the δ1 methyl group of Leucine are observable.

The compound of formula 3 enables to specifically label with $^{12}CH_3$ γ2 methyl groups of Ile. This compound enables to perform structural studies, specific attribution and detection of weak dipolar and scalar interactions by NMR in proteins of less than 30 kDa.

The labeling of the γ2 methyl groups of Ile with the compound of formula 3 (2-($^2H_5$)ethyl-2-hydroxy-3-oxobutanoic acid) is shown in the following schema:

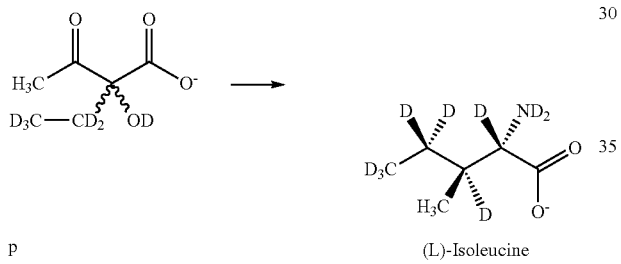

It enables to perform structural studies, by liquid NMR, of proteins and biomolecular assemblies.

The compound of formula 4 enables to stereospecifically label with $^{13}CH_3$ proS methyl groups of Valine (γ2 methyl) and proS methyl groups of Leucine (δ2 methyl). It enables to perform structural studies by liquid NMR of proteins and large biomolecular assemblies.

The stereospecific labeling of proS methyl groups of Valine and Valine with the compound of formula 4 (2-hydroxy-2-($^{13}C$)methyl-3-oxo-4($^2H_3$)butanoic acid) is shown to the following schema:

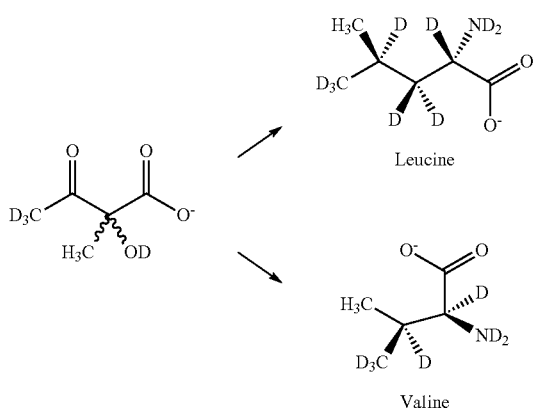

When the compound of formula 4 is used for stereospecifically labeling TET2 (U—[$^2H$], U—[$^{12}C$], Leu/Val-[$^{13}C^1H3$]$^{proS}$ TET2) a dodecameric protease of 468 kDa and malate synthase G (MSG) (U—[$^2H$], U—[$^{12}C$], Leu/Val-[$^{13}C^1H3$]$^{proS}$ MSG) produced using E. coli cells in a deuterated M9 medium in presence of 300 mg/L of the compound of formula 4, the methyl-TROSY spectra of the obtained compounds show that only half of the resonances of the methyl groups are observable.

The compound of formula 5 (2-hydroxy-2-($^2H_3$)methyl-3-oxo-4($^{13}C$)butanoic acid) enables to stereospecifically label with $^{13}CH_3$ proR methyl group of the Valines (γ1 methyl) and proR methyl group of the Leucines (δ1 methyl).

It enables to perform structural studies by liquid NMR of proteins and large biomolecular assemblies.

The labeling with this compound of formula 5 leads to labeled amino acids Leucine and Valine as shown to the following schema:

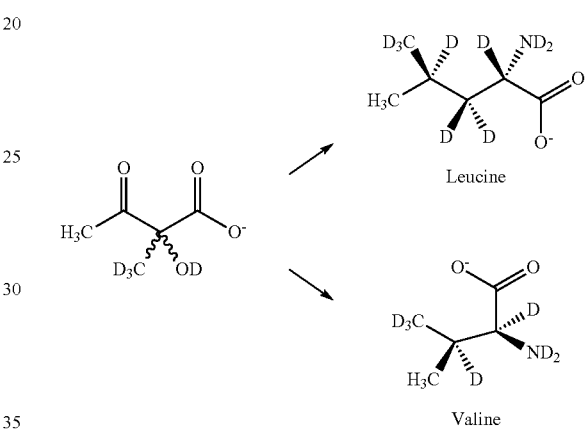

When this compound of formula 5 is used for obtaining TET2 (U—[$^2H$], U—[$^{12}C$], Leu/Val-[$^{13}C^1H_3$]$^{proR}$ TET2), a dodecameric protease of 468 kDa produced using E. coli cells in a deuterated M9 medium in presence of 300 mg/L of the compound of formula 5, the methyl-TROSY spectra of the obtained compound shows only half of the resonance of the methyl groups as compared to the spectra of TET2 produced from isovalerate which is protonated on the two methyl groups.

The compound of formula 6 (2-($^2H_5$)ethyl-2-hydroxy-3-oxo-4($^{13}C$)methylbutanoic acid) enables to label with $^{13}CH_3$ γ2 methyl groups of Isoleucine.

It enables to perform structural studies by liquid NMR of proteins and large biomolecular assemblies.

This compound leads to (L)-Isoleucine labeled as shown in the following schema.

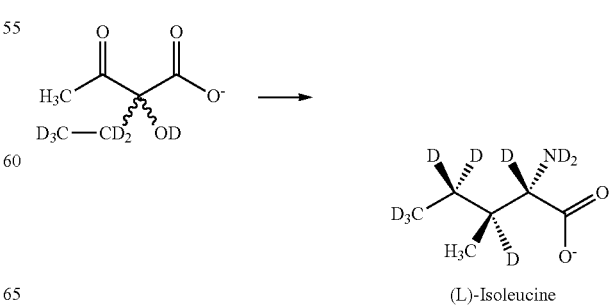

The methyl-TROSY spectra of TET2 (U-[$^2$H], U—[$^{12}$C], Ile-[$^{13}$C$^1$H$_3$]$^{\gamma 2}$ TET2), a dodecameric protease of 468 kDa produced in a deuterated M9 medium in presence of 300 mg/L of the compound of formula 6 shows only γ2 methyl groups of Isoleucine.

The compound of formula 7 (U—($^{13}$C)-2-hydroxy-2-methyl-3-oxo-4-($^2$H$_3$)butanoic acid) enables to stereoselectively assign the proS methyl groups of Valine (γ2 methyl) and proS methyl groups of Leucine (δ2 methyl) in proteins and large biomolecular assemblies by liquid NMR.

This compound leads to the following labeling of Leucine and Valine:

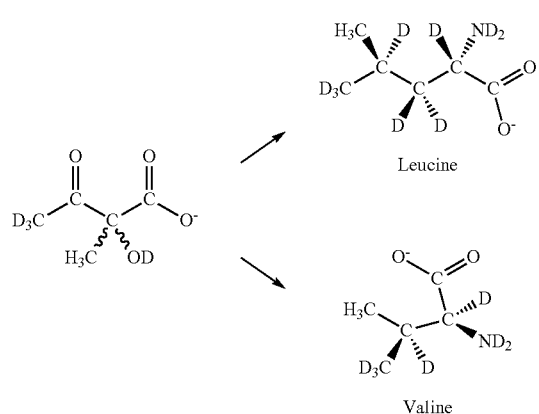

Leucine

Valine

The compound of formula 8 (U—($^{13}$C)-2-hydroxy-2-($^2$H$_3$)methyl-3-oxobutanoic acid) enables stereoselectively assign the proR methyl groups of Valine (γ1 methyl) and proR methyl groups of Leucine (δ1 methyl) in proteins and large biomolecular assemblies by liquid NMR.

The compound of formula 8 gives the following labeling of Leucine and Valine amino acids in proteins and biomolecular assemblies:

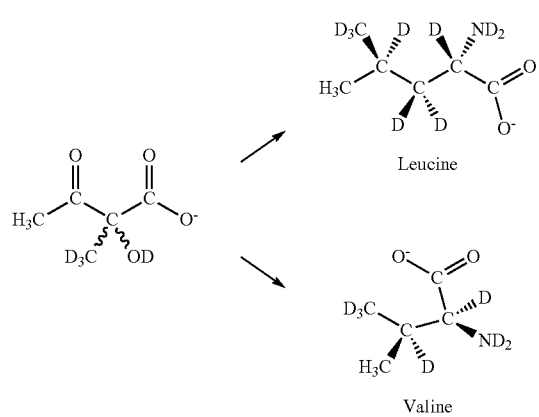

Leucine

Valine

The compound of formula 9 (1,2,3,4-($^{13}$C)-2-($^2$H$_5$)ethyl-2-hydroxy-3-oxobutanoic acid) enables to assign the γ2 methyl groups of Isoleucine in proteins and biomolecular assemblies by liquid NMR.

Isoleucine is labeled as shown below:

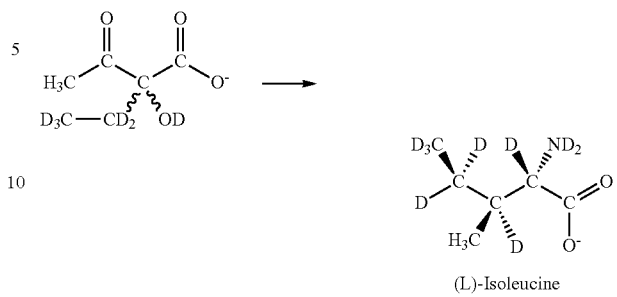

(L)-Isoleucine

The compound of formula 10 (2-hydroxy-2-($^2$H, $^{13}$C) methyl-3-oxo-4-($^2$H$_3$)butanoic acid) enables to stereospecifically label with $^{13}$CDH$_2$ proS methyl groups of Valine (γ2 methyl) and proS methyl groups of Leucine (δ2 methyl).

It can be used for $^2$H dynamic studies of proteins by liquid NMR.

The schema below shows how the amino acids Leucine and Valine are labeled with this compound of formula 10.

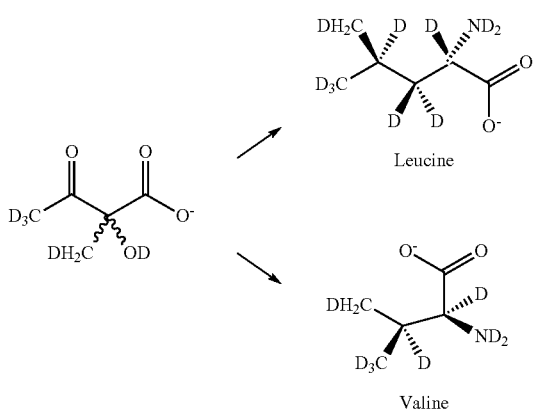

Leucine

Valine

The compound of formula 11 (2-hydroxy-2-($^2$H$_3$)methyl-3-oxo-4-($^2$H, $^{13}$C)butanoic acid) enables to stereospecifically label with $^{13}$CDH$_2$ proR methyl groups of Valine (γ1 methyl) and proR methyl groups of Leucine (δ1 methyl).

It can be used for $^2$H dynamic studies of proteins by liquid NMR. This compound labels the amino acids Leucine and Valine in the manner shown in the following schema:

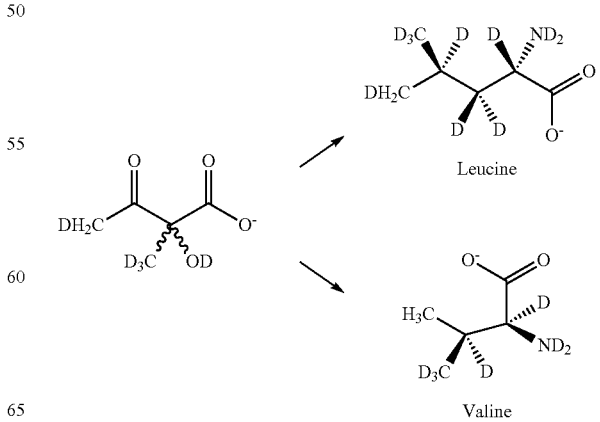

Leucine

Valine

The compound of formula 12 (2-($^2$H$_5$)ethyl-2-hydroxy-3-oxo-4-($^2$H, $^{13}$C)butanoic acid) enables to specifically label with $^{13}$CDH$_2$ γ2 methyl groups of Isoleucine.

It can be used for $^2$H dynamic studies of proteins by liquid NMR.

The compound of formula 12 label (L)-Isoleucine as shown in the following schema:

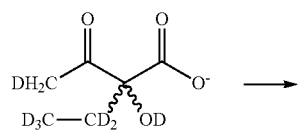

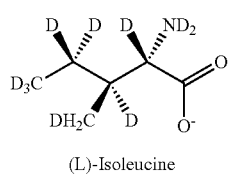

(L)-Isoleucine

The compound of formula 13 (2-hydroxy-2-($^2$H$_2$, $^{13}$C) methyl-3-oxo-4-($^2$H$_3$)butanoic acid) enables to stereospecifically label with $^{13}$CHD$_2$ proS methyl groups of Valine (γ2 methyl) and proS methyl groups of Leucine (δ2 methyl).

It can be used for solid state NMR of proteins and dynamic studies of proteins by liquid NMR.

The following schema shows how compound 13 labels Leucine and Valine in proteins:

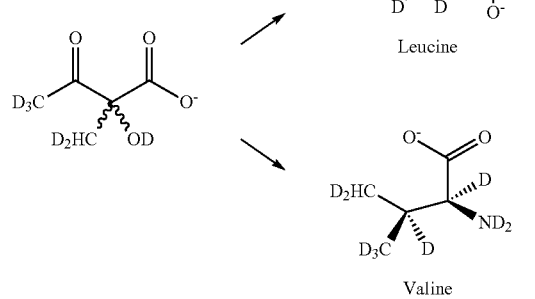

The compound of formula 14 (2-hydroxy-2-($^2$H$_3$)methyl-3-oxo-4-($^2$H$_2$, $^{13}$C)butanoic acid) enables to stereospecifically label with $^{13}$CHD$_2$ proR methyl groups of Valine (γ1 methyl) and proR methyl groups of Leucine (δ1 methyl).

It can be used for solid state NMR of proteins and for dynamic studies of proteins by liquid NMR.

This compound labels Leucine and Valine as shown in the following schema:

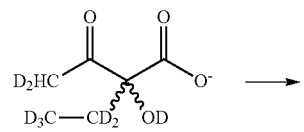

Leucine

Valine

The compound of formula 15 (2-($^2$H$_5$)ethyl-2-hydroxy-3-oxo-4-($^2$H$_2$, $^{13}$C)butanoic acid) enables to label with $^{13}$CHD$_2$ specifically γ2 methyl groups of Isoleucine in proteins.

It can be used for solid state NMR of proteins and for dynamic studies of proteins by liquid NMR.

This compound labels Isoleucine as shown in the following schema:

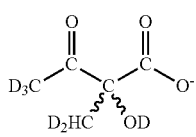

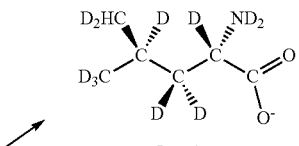

(L)-Isoleucine

The compound of formula 16 (U—($^{13}$C)-2-hydroxy-2-($^2$H$_2$)methyl-3-oxo-4-($^2$H$_3$)butanoic acid) can be used for solid state NMR of proteins.

It allows to label the carbon chain of Valine and Leucine and with $^{13}$CHD$_2$ the proS methyl groups of Valine (γ2 methyl) and proS methyl groups of Leucine (δ2 methyl) in proteins as shown in the following schema:

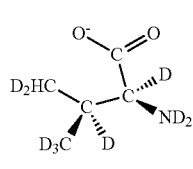

Leucine

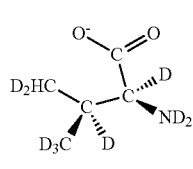

Valine

The compound of formula 17 (U—($^{13}$C)-2-hydroxy-2-($^2$H$_3$)methyl-3-oxo-4-($^2$H$_2$)butanoic acid) can be used for solid state NMR of proteins.

It enables to label the carbon chain of Leucine and Valine and with $^{13}$CHD$_2$ the proR methyl groups of Valine (γ1 methyl) and proR methyl groups of Leucine (δ1 methyl) in protein as shown in the following schema:

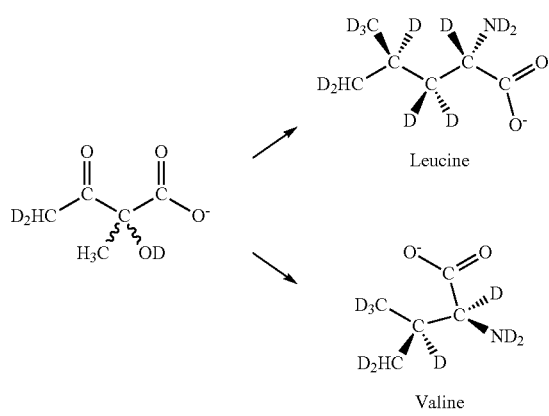

Leucine

Valine

The compound of formula 18 (1,2,3,4-($^{13}$C)-2-($^2$H$_5$)ethyl-2-hydroxy-3-oxo-4-($^2$H$_2$)butanoic acid) can be used for solid state NMR of proteins It enables to label the carbon chain and with $^{13}$CHD$_2$ the γ2 methyl groups of Isoleucine in proteins as shown in the following schema:

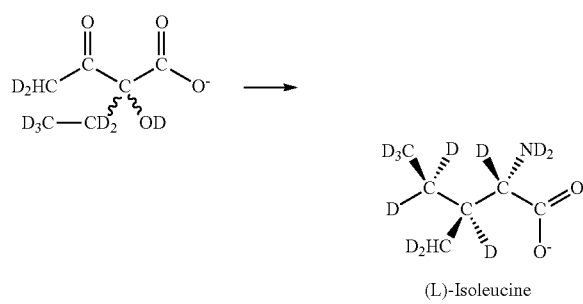

(L)-Isoleucine

To summarize, among the acetolactate derivatives of formula I:

1) those more appropriate for assignment of NMR signals and/or measurements of structural restraints have the following formulae:
4=2-hydroxy-2-($^{13}$C)methyl-3-oxo-4($^2$H$_3$)butanoic acid,
5=2-hydroxy-2-($^2$H$_3$)methyl-3-oxo-4($^{13}$C)butanoic acid,
6=2-($^2$H$_5$)ethyl-2-hydroxy-3-oxo-4-($^{13}$C)methylbutanoic acid,
9=1,2,3,4-($^{13}$C)-2-($^2$H$_5$)ethyl-2-hydroxy-3-oxobutanoic acid,
21=1,2,3-($^{13}$C)-2-($^{13}$C)methyl-2-hydroxy-3-oxo-4-($^2$H$_3$)butanoic Acid,
22=1,2,3,4-($^{13}$C)-2-($^2$H$_3$)methyl-2-hydroxy-3-oxobutanoic acid,
24=1,2,3-($^{13}$C)-2-(1'-($^2$H$_2$), $^{13}$C$_2$)ethyl)-2-hydroxy-3-oxo-4-($^2$H$_3$)butanoic acid,
36=3,4-($^{13}$C)-2-($^{13}$C)methyl-2-hydroxy-3-oxo-4-($^2$H$_3$)butanoic acid,
37=3,4-($^{13}$C)-2-($^2$H$_3$, $^{13}$C)methyl-2-hydroxy-3-oxobutanoic acid 40=3,4-($^{13}$C)-2-($^{13}$C)methyl-2-hydroxy-3-oxobutanoic acid,
45=3,4-($^{13}$C)-2-(1'-($^2$H$_2$),$^{13}$C$_2$)ethyl-2-hydroxy-3-oxo-4-($^2$H$_3$)butanoic acid,
46=3,4-($^{13}$C)-2-($^2$H$_5$, $^{13}$C$_2$)ethyl-2-hydroxy-3-oxobutanoic acid,
49=3,4-($^{13}$C)-2-(1'-($^2$H$_2$),$^{13}$C$_2$)ethyl-2-hydroxy-3-oxobutanoic acid.

2) those which are preferably used for dynamics studies by liquid state NMR and for use in solid state NMR are the compounds of the following formulae:
13=2-hydroxy-2-($^2$H$_2$, $^{13}$C)methyl-3-oxo-4-($^2$H$_3$)butanoic acid,
14=2-hydroxy-2-($^2$H$_3$)methyl-3-oxo-4-($^2$H$_2$, $^{13}$C)butanoic acid,
15=2-($^2$H$_5$)ethyl-2-hydroxy-3-oxo-4-($^2$H$_2$, $^{13}$C)butanoic acid,
34=2-(1'-($^2$H$_2$),2'-($^2$H),2'-($^{13}$C))ethyl-2-hydroxy-3-oxo-4-($^2$H$_3$)butanoic acid, and 3) for dynamics studies by $^2$H NMR, preferred acetolactate derivatives of formula I have the following formulae:
10=2-hydroxy-2-($^2$H, $^{13}$C)methyl-3-oxo-4-($^2$H$_3$)butanoic acid,
11=2-hydroxy-2-($^2$H$_3$)methyl-3-oxo-4-($^2$H, $^{13}$C)butanoic acid,
12=2-($^2$H$_5$)ethyl-2-hydroxy-3-oxo-4-($^2$H, $^{13}$C)butanoic acid.

The labeling process of the invention was applied to malate synthase G (MSG), the largest monomeric protein (82 kDa) for which a 3 D structure has been determined by NMR spectroscopy, using compound of formula 4.

The methyl-TROSY spectra of specifically protonated MSG over expressed in E. Coli in the presence of the compound 4 of the invention have been compared with those of MSG over expressed in E. Coli in the presence of 2-oxo-3-($^2$H$_3$)-3-($^2$H)-4-($^{13}$C)-ketoisovalerate.

A direct comparison of these spectra shows that replacing α-ketoisovalerate with compound of the invention increases the sensitivity of NMR spectra by a factor of 1.6 (theoritically 2) and decreases the number of peaks by two.

Only signals for Val-γ$_2$ and Leu-δ$_2$ methyl groups can be observed when the protein is prepared using synthetic 2-($^{13}$C)methyl-4-($^2$H$_3$)-acetolactate (compound of formula 4).

The absence of signals for Val-γ$_1$ and Leu-δ$_1$ methyl groups confirms that the $^{13}$C$^1$H$_3$ methyl substituent in position 2 of 2-(S)-acetolactate is stereospecifically transferred in-vivo to position proS of 2,3-dihydroxy-isovalerate by ketol-isomerase and that no methyl interconversion occurs in the following steps of the Leu/Val biosynthetic pathway.

Furthermore, no signals for CH$_2$D and CD$_2$H isotopomers were detected demonstrating that H/D exchange does not occur after the introduction of acetolactate to M9/D$_2$O culture medium. Lastly, no scrambling to other methine, methylene or methyl sites was detected, indicating that the excess of acetolactate in-vivo does not interfere with other metabolic pathways.

Thus, the use of specifically-labeled acetolactate is an efficient method to realize a complete and stereospecific methyl-labeling of Leu and Val side chains in a fully perdeuderated protein background without detectable scrambling.

As the acetolactate derivatives are not incorporated into other metabolic pathways, they can be conveniently used in combination with other precursors such as those proposed for specific labeling of Ile-[CH$_3$]$^{δ□□}$, or Ala-[CH$_3$]$^β$ methyl groups.

An obvious first application of this new labeling scheme is the stereospecific assignment of methyl groups of Leu, Val and Ile.

Despite the existence of efficient methods to connect methyl resonances to sequentially-assigned backbone nuclei, the stereospecific assignment of prochiral methyl groups remains difficult. Previous approaches have involved either a fractional [$^{13}$C]-labeling strategy or the measurement of small scalar couplings.

While these approaches have been shown to be useful for small and medium size proteins, their application to larger proteins is challenging. In comparison, stereospecific assignment of Leu, Val, and Ile methyl groups can be obtained directly by visually inspecting 2D methyl-TROSY spectra recorded on specifically protonated proteins produced with compound of formula 4 according to the invention.

This strategy is directly applicable to large proteins as demonstrated for MSG (82 kDa) for which 98% of Leu/Val methyl groups were unambiguously assigned stereospecifically.

Specific protonation of methyl groups is a powerful method to extract long-range distance restraints in proteins.

For large proteins the extraction of inter-methyl NOE is generally hampered by the low intrinsic resolution of $^{13}$C-edited 4D NOESY spectra.

Simplification of spectra using the stereospecific labeling of prochiral methyl groups according to the process of the invention significantly reduces ambiguity in the analysis of Nuclear Over Hauser effect (NOE) cross peaks.

NOEs between proS and proR methyl groups are no longer detected using stereospecifically-labeled samples. However, the use of the compound 4 of the invention in place of 2-oxo-3-($^2$H$_3$)-3-($^2$H)-4-($^{13}$C)-ketoisovalerate increases the protonation level of proS methyl groups theoretically two-fold, which in turn enhances the intensity of the remaining NOE cross-peaks by a factor of theoretically 4.

This gain in sensitivity leads to the detection of new structurally meaningful long-range NOE cross-peaks between more remote proS methyl groups, thereby compensating for the loss of NOEs involving proR methyl groups.

A comparison of distance restraints extracted from 4D NOESY spectra revealed that stereospecific labeling of Leu/Val methyl groups increased the distance threshold for which an NOE can be detected by ~20%. Prochiral-specific labeling of methyl groups is not only an attractive way to simplify the time-consuming step of NOE analysis, it allows a significant extension of the range of structurally meaningful $^1$H-$^1$H distances that can be measured in large proteins.

The process of this invention can also be used for the specific isotopic labeling of amino acids selected from the group consisting of Val, Leu and Ile, and more particularly for the specific labeling of methyl groups of Leu and Val as well as specific labeling of the γ2-methyl groups of isoleucine.

Another object of the invention is acetolactate derivatives of the following formula I-1:

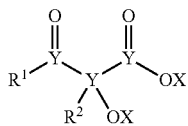

Formula I-1 wherein:

X is an exchangeable hydrogen being $^1$H or $^2$H (D) depending on the nature of the solvent, each Y is independently from the others $^{12}$C or $^{13}$C, R$^1$ is a methyl group in which the carbon atom is $^{13}$C or $^{12}$C and the hydrogen atoms are independently from each other $^1$H or $^2$H (D), R$^2$ is either a methyl group in which the carbon atom is $^{13}$C or $^{12}$C and the hydrogen atoms are independently from each other $^1$H or $^2$H (D), or an ethyl group in which the carbon atoms are independently from each other $^{13}$C or $^{12}$C and the hydrogen atoms are independently from each other $^1$H or $^2$H (D), at the provisos that:

1) the hydrogen atoms of the acetolactate derivative of Formula I are not all, at the same time, either $^1$H or $^2$H (D), 2) the hydrogen atoms of R$^1$ and the hydrogen atoms of R$^2$ are not all, at the same time, either $^1$H or $^2$H (D), 3) when all the hydrogen atoms of R$^1$ are $^2$H, then the carbon atoms, in formula I-1, are not all, at the same time, $^{12}$C.

Preferred compounds of the invention have the formula I-1 in which:

R$^1$ is chosen among the following groups:
$^{12}$CH$_3$, $^{12}$CD$_3$, $^{13}$CH$_3$, $^{13}$CD$_3$, $^{13}$CHD$_2$, $^{13}$CH$_2$D, R$^2$ is chosen among the following groups:
$^{12}$CH$_3$, $^{12}$CD$_3$, $^{13}$CH$_3$, $^{13}$CD$_3$, $^{13}$CHD$_2$, $^{13}$CH$_2$D, $^{12}$CH$_3$$^{12}$CD$_2$, $^{12}$CD$_3$$^{12}$CD$_2$, $^{13}$CH$_3$$^{12}$CD$_2$, $^{13}$CH$_3$$^{13}$CD$_2$, $^{13}$CD$_3$$^{13}$CD$_2$, $^{13}$CHD$_2$$^{13}$CD$_2$, $^{13}$CH$_2$D$^{13}$CD$_2$, $^{13}$CHD$_2$$^{12}$CD$_2$, $^{13}$CH$_2$D$^{12}$CD$_2$, each Y is independently from the others $^{12}$C or $^{13}$C, at the provisos that:

1) the hydrogen atoms of the acetolactate derivative of Formula I are not all, at the same time, either $^1$H or $^2$H (D), 2) the hydrogen atoms of R$^1$ and the hydrogen atoms of R$^2$ are not all, at the same time, either $^1$H or $^2$H (D), and 3) when all the hydrogen atoms of R$^1$ are $^2$H, then the carbon atoms, in formula I-1 are not all, at the same time, $^{12}$C.

Preferred compounds of the invention are the compounds of following formulae 2-57:

2=2-hydroxy-2-($^2$H$_3$)methyl-3-oxobutanoic acid,
3=2-($^2$H$_5$)ethyl-2-hydroxy-3-oxobutanoic acid,
4=2-hydroxy-2-($^{13}$C)methyl-3-oxo-4($^2$H$_3$)butanoic acid,
5=2-hydroxy-2-($^2$H$_3$)methyl-3-oxo-4($^{13}$C)butanoic acid,
6=2-($^2$H$_5$)ethyl-2-hydroxy-3-oxo-4-($^{13}$C)methylbutanoic acid,
7=U—($^{13}$C)-2-hydroxy-2-methyl-3-oxo-4($^2$H$_3$)butanoic acid,
8=U—($^{13}$C)-2-hydroxy-2-($^2$H$_3$)methyl-3-oxobutanoic acid,
9=1,2,3,4-($^{13}$C)-2-($^2$H$_5$)ethyl-2-hydroxy-3-oxobutanoic acid,
10=2-hydroxy-2-($^2$H, $^{13}$C)methyl-3-oxo-4-($^2$H$_3$)butanoic acid,
11=2-hydroxy-2-($^2$H$_3$)methyl-3-oxo-4-($^2$H, $^{13}$C)butanoic acid,
12=2-($^2$H$_5$)ethyl-2-hydroxy-3-oxo-4-($^2$H, $^{13}$C)butanoic acid,
13=2-hydroxy-2-($^2$H$_2$, $^{13}$C)methyl-3-oxo-4-($^2$H$_3$)butanoic acid,
14=2-hydroxy-2-($^2$H$_3$)methyl-3-oxo-4-($^2$H$_2$, $^{13}$C)butanoic acid,
15=2-($^2$H$_5$)ethyl-2-hydroxy-3-oxo-4-($^2$H$_2$, $^{13}$C)butanoic acid,
16=U—($^{13}$C)-2-hydroxy-2-($^2$H$_2$)methyl-3-oxo-4-($^2$H$_3$)butanoic acid, 17=U—($^{13}$C)-2-hydroxy-2-($^2$H$_3$)methyl-3-oxo-4-($^2$H$_2$)butanoic acid,
18=1,2,3,4-($^{13}$C)-2-(2H$_5$)ethyl-2-hydroxy-3-oxo-4-($^2$H$_2$)butanoic acid,
19=2-(1'-($^2$H$_2$)ethyl-2-hydroxy-3-oxo-4-($^2$H$_3$)butanoic acid,
20=2-((1'-($^2$H$_2$),2'-($^{13}$C))ethyl-2-hydroxy-3-oxo-4-($^2$H$_3$)butanoic acid,
21=1,2,3-($^{13}$C)-2-($^{13}$C)methyl-2-hydroxy-3-oxo-4-($^2$H$_3$)butanoic acid,
22=1,2,3,4-($^{13}$C)-2-($^2$H$_3$)methyl-2-hydroxy-3-oxobutanoic acid,
23=U—($^{13}$C)-2-($^2$H$_5$)ethyl-2-hydroxy-3-oxobutanoic acid,
24=1,2,3-($^{13}$C)-2-(1'-($^2$H$_2$), $^{13}$C$_2$)ethyl)-2-hydroxy-3-oxo-4-($^2$H$_3$)butanoic acid,
25=U—($^{13}$C)-2-(1'-($^2$H$_2$))ethyl-2-hydroxy-3-oxo-4-($^2$H$_3$)butanoic acid,
26=U—($^{13}$C)-2-($^2$H)methyl-2-hydroxy-3-oxo-4-($^2$H$_3$)butanoic acid,
27=U—($^{13}$C)-2-($^2$H$_3$)methyl-2-hydroxy-3-oxo-4-($^2$H)butanoic acid,
28=U—($^{13}$C)-2-(($^2$H$_5$)ethyl)-2-hydroxy-3-oxo-4-($^2$H)butanoic acid,
29=1,2,3-($^{13}$C)-2-($^2$H, $^{13}$C)methyl-2-hydroxy-3-oxo-4-($^2$H$_3$)butanoic acid,
30=1,2,3,4-($^{13}$C)-2-($^2$H$_3$)methyl-2-hydroxy-3-oxo-4-($^2$H)butanoic acid,
31=1,2,3,4-($^{13}$C)-2-($^2$H$_5$)ethyl-2-hydroxy-3-oxo-4-($^2$H)butanoic acid,
32=U—($^{13}$C)-2-(1'-($^2$H$_2$),2'-($^2$H))ethyl-2-hydroxy-3-oxo-4-($^2$H$_3$)butanoic acid,
33=1,2,3-($^{13}$C)-2-(2'-($^2$H), $^{13}$C$_2$)ethyl-2-hydroxy-3-oxo-4-($^2$H$_3$)butanoic acid,
34=2-(1'-($^2$H$_2$),2'-($^2$H),2'-($^{13}$C))ethyl-2-hydroxy-3-oxo-4-($^2$H$_3$)butanoic acid,
35=1,2,3-($^{13}$C)-2-($^2$H$_2$, $^{13}$C)methyl-2-hydroxy-3-oxo-4-($^2$H$_3$)butanoic acid,
36=3,4-($^{13}$C)-2-($^{13}$C)methyl-2-hydroxy-3-oxo-4-($^2$H$_3$)butanoic acid,
37=3,4-($^{13}$C)-2-($^2$H$_3$, $^{13}$C)methyl-2-hydroxy-3-oxobutanoic acid,
38=3,4-($^{13}$C)-2-($^2$H$_2$, $^{13}$C)methyl-2-hydroxy-3-oxo-4-($^2$H$_3$)butanoic acid,
39=3,4-($^{13}$C)-2-($^2$H, $^{13}$C)methyl-2-hydroxy-3-oxo-4-($^2$H$_3$)butanoic acid,
40=3,4-($^{13}$C)-2-($^{13}$C)methyl-2-hydroxy-3-oxobutanoic acid,
41=3,4-($^{13}$C)-2-($^2$H, $^{13}$C)methyl-2-hydroxy-3-oxo-4-($^2$H)butanoic acid,
42=3,4-($^{13}$C)-2-($^2$H$_2$, $^{13}$C)methyl-2-hydroxy-3-oxo-4-($^2$H$_2$)butanoic acid,
43=3,4-($^{13}$C)-2-($^2$H$_3$, $^{13}$C)methyl-2-hydroxy-3-oxo-4-($^2$H$_2$)butanoic acid,
44=3,4-($^{13}$C)-2-($^2$H$_3$, $^{13}$C)methyl-2-hydroxy-3-oxo-4-($^2$H)butanoic acid,
45=3,4-($^{13}$C)-2-(1'-($^2$H$_2$),$^{13}$C$_2$)ethyl-2-hydroxy-3-oxo-4-($^2$H$_3$)butanoic acid,
46=3,4-($^{13}$C)-2-($^2$H$_5$, $^{13}$C$_2$)ethyl-2-hydroxy-3-oxobutanoic acid,
47=3,4-($^{13}$C)-2-(1'-($^2$H$_2$),2'-($^2$H),$^{13}$C$_2$)ethyl-2-hydroxy-3-oxo-4-($^2$H$_3$)butanoic acid,
48=3,4-($^{13}$C)-2-(1'-($^2$H$_2$),2'-($^2$H$_2$),$^{13}$C$_2$)ethyl-2-hydroxy-3-oxo-4-($^2$H$_3$)butanoic acid,
49=3,4-($^{13}$C)-2-(1'-($^2$H$_2$),$^{13}$C$_2$)ethyl-2-hydroxy-3-oxobutanoic acid,
50=3,4-($^{13}$C)-2-(1'-($^2$H$_2$),2'-($^2$H$_2$),$^{13}$C$_2$)ethyl-2-hydroxy-3-oxo-4-($^2$H$_2$)butanoic acid,
51=3,4-($^{13}$C)-2-(1'-($^2$H$_2$)-2'-($^2$H),$^{13}$C$_2$)ethyl-2-hydroxy-3-oxo-4-($^2$H)butanoic acid,
52=3,4-($^{13}$C)-2-(2H$_5$, $^{13}$C$_2$)ethyl-2-hydroxy-3-oxo-4-($^2$H$_2$)butanoic acid,
53=3,4-($^{13}$C)-2-(2H$_5$, $^{13}$C$_2$)ethyl-2-hydroxy-3-oxo-4-($^2$H)butanoic acid,
54-U—($^{13}$C)-2-($^2$H$_5$)ethyl-2-hydroxy-3-oxo-4-($^2$H$_2$)butanoic acid,
55-U—($^{13}$C)-2-($^2$H$_5$)ethyl-2-hydroxy-3-oxo-4-($^2$H)butanoic acid,
56=1,2,3-($^{13}$C)-2-(1'-($^2$H$_2$),2'-($^2$H$_2$),$^{13}$C$_2$)ethyl-2-hydroxy-3-oxo-4-($^2$H$_3$)butanoic acid,
57=U—($^{13}$C)-2-(1'-($^2$H$_2$),2'-($^2$H$_2$))ethyl-2-hydroxy-3-oxo-4-($^2$H$_3$)butanoic acid.

Among these compounds, the compounds of the following formulae are preferred:
4=2-hydroxy-2-($^{13}$C)methyl-3-oxo-4($^2$H$_3$)butanoic acid,
5=2-hydroxy-2-($^2$H$_3$)methyl-3-oxo-4($^{13}$C)butanoic acid,
6=2-($^2$H$_5$)ethyl-2-hydroxy-3-oxo-4-($^{13}$C)methylbutanoic acid,
9=1,2,3,4-($^{13}$C)-2-($^2$H$_5$)ethyl-2-hydroxy-3-oxobutanoic acid,
21=1,2,3-($^{13}$C)-2-($^{13}$C)methyl-2-hydroxy-3-oxo-4-($^2$H$_3$)butanoic Acid,
22=1,2,3,4-($^{13}$C)-2-($^2$H$_3$)methyl-2-hydroxy-3-oxobutanoic acid,
24=1,2,3-($^{13}$C)-2-(1'-($^2$H$_2$), $^{13}$C$_2$)ethyl)-2-hydroxy-3-oxo-4-($^2$H$_3$)butanoic acid,
36=3,4-($^{13}$C)-2-($^{13}$C)methyl-2-hydroxy-3-oxo-4-($^2$H$_3$)butanoic acid,
37=3,4-($^{13}$C)-2-($^2$H$_3$, $^{13}$C)methyl-2-hydroxy-3-oxobutanoic acid
40=3,4-($^{13}$C)-2-($^{13}$C)methyl-2-hydroxy-3-oxobutanoic acid,
45=3,4-($^{13}$C)-2-(1'-($^2$H$_2$),$^{13}$C$_2$)ethyl-2-hydroxy-3-oxo-4-($^2$H$_3$)butanoic acid,
46=3,4-($^{13}$C)-2-($^2$H$_5$, $^{13}$C$_2$)ethyl-2-hydroxy-3-oxobutanoic acid,
49=3,4-($^{13}$C)-2-(1'-($^2$H$_2$),$^{13}$C$_2$)ethyl-2-hydroxy-3-oxobutanoic acid.

But still other preferred compounds have the following formulae:
13=2-hydroxy-2-($^2$H$_2$, $^{13}$C)methyl-3-oxo-4-($^2$H$_3$)butanoic acid,
14=2-hydroxy-2-($^2$H$_3$)methyl-3-oxo-4-($^2$H$_2$, $^{13}$C)butanoic acid,
15=2-($^2$H$_5$)ethyl-2-hydroxy-3-oxo-4-($^2$H$_2$, $^{13}$C)butanoic acid,
34=2-(1'-($^2$H$_2$),2'-(2H),2'-($^{13}$C))ethyl-2-hydroxy-3-oxo-4-($^2$H$_3$)butanoic acid.

Other preferred acetolactate derivatives according to the invention have the following formulae:
10=2-hydroxy-2-($^2$H, $^{13}$C)methyl-3-oxo-4-($^2$H$_3$)butanoic acid,
11=2-hydroxy-2-($^2$H$_3$)methyl-3-oxo-4-($^2$H, $^{13}$C)butanoic acid,
12=2-($^2$H$_5$)ethyl-2-hydroxy-3-oxo-4-($^2$H, $^{13}$C)butanoic acid.

The invention also proposes a process for manufacturing a compound of formula I, more particularly of formula 1-18, which comprises the following steps:

a) alkylation, with a methyl group in which the carbon atom is $^{13}$C or $^{12}$C and the hydrogen atoms are independently from each other $^1$H or $^2$H (D), or an ethyl group in which the carbon atoms are independently from each other $^{13}$C or $^{12}$C and the hydrogen atoms are independently from each other $^1$H or $^2$H (D), of 3-oxobutanoate having its hydroxyl group in position 1 protected by a protecting group, preferably a methyl or ethyl group, b) hydroxylation of the compound obtained in step a), c) optionally deprotection and exchange of the desired $^1$H atoms by $^2$H atoms, wherein step b) of hydroxylation is carried out by using dimethyldioxirane in presence of Nickel (II) ions.

Step b) of hydroxylation according to the process of the invention, enables to improve the total yield of the process to more than 90% whereas when this hydroxydation step is carried out using molecular oxygen in presence of Cobalt or Cerium ions as a catalyst, as suggested by the prior art, the total yield of the process is only of about 50% without any other steps are modified.

The labeling process of the invention is particularly appropriate for analysing proteins, including those included in biomolecular assemblies by NMR.

Thus, the invention also proposes processes for analysing proteins by NMR.

In a first embodiment, this process comprises a step of labeling of proteins to be analysed by the process of labeling of the invention.

In a second embodiment, this process comprises a step of labeling of proteins to be analysed with a compound if the following formula I:

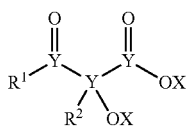

Formula I wherein:
X is $^1$H or $^2$H (D),
each Y is independently from the others $^{12}$C or $^{13}$C,
$R^1$ is a methyl group in which the carbon atom is $^{13}$C or $^{12}$C and the hydrogen atoms are independently from each other $^1$H or $^2$H (D),
$R^2$ is either a methyl group in which the carbon atom is $^{13}$C or $^{12}$C and the hydrogen atoms are independently from each other $^1$H or $^2$H (D), or an ethyl group in which the carbon atoms are independently from each other $^{13}$C or $^{12}$C and the hydrogen atoms are independently from each other $^1$H or $^2$H (D),
at the provisos that:
1) the hydrogen atoms of the acetolactate derivative of Formula I are not all, at the same time, either $^1$H or $^2$H (D),
2) the hydrogen atoms of $R^1$ and the hydrogen atoms of $R^2$ are not all, at the same time, either $^1$H or $^2$H (D).

In a third embodiment, this process comprises a step of labeling of proteins to be analysed with a compound if the following formula I-1:

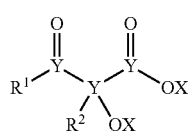

Formula I-1 wherein:
X is $^1$H or 2H (D),
each Y is independently from the others $^{12}$C or $^{13}$C, $R^1$ is a methyl group in which the carbon atom is $^{13}$C or $^{12}$C and the hydrogen atoms are independently from each other $^1$H or $^2$H (D),
$R^2$ is either a methyl group in which the carbon atom is $^{13}$C or $^{12}$C and the hydrogen atoms are independently from each other $^1$H or $^2$H (D), or an ethyl group in which the carbon atoms are independently from each other $^{13}$C or $^{12}$C and the hydrogen atoms are independently from each other $^1$H or $^2$H (D),
at the provisos that:
1) the hydrogen atoms of the acetolactate derivative of Formula I are not all, at the same time, either $^1$H or $^2$H (D),
2) the hydrogen atoms of $R^1$ and the hydrogen atoms of $R^2$ are not all, at the same time, either $^1$H or $^2$H (D),
3) when all the hydrogen atoms of $R^1$ are $^2$H, then the carbon atoms, in formula I-1, are not all, at the same time, $^{12}$C.

In order that the invention be better understood, an example of carrying out the labeling process of the invention is given below. This example is only illustrative, and in no way limitative of the invention.

1. Synthesis of Selectively Methyl-Labeled Acetolactate

Ethyl 2-($^{13}$C)methyl-3-oxobutanoate

A mixture of 12.15 mL (95.4 mmol) of ethyl 3-oxobutanoate (A), 14.5 g (104.9 mmol) $K_2CO_3$ and 15.0 g (104.9 mmol) $^{13}$C-methyl iodide (Cambridge Isotope Laboratories, Inc.) in 120 mL of absolute ethanol was heated at 40° C. under argon for 90 h. After filtration, the filtrate was concentrated in vacuo to afford 12.30 g (yield 89%) of product, which was sufficiently pure to be used without further purification. $^1$H NMR (CDCl$_3$); 4.21 (q, J=7.1 Hz, 2H), 3.51 (dq, J=7.2, 4.4 Hz, 1H), 2.25 (s, 3H), 1.35 (dd, J=130.4, 7.2 Hz, 3H), 1.29 (t, J=7.1 Hz, 3H).

Ethyl 2-hydroxy-2-($^{13}$C)methyl-3-oxobutanoate (B)

Hydroxylation reaction was carried out by freshly prepared dimethyldioxirane in presence of Nickel(II) ions. To a mixture of 50 mg (0.345 mmol) of ethyl 2-($^{13}$C)methyl-3-oxobutanoate in 3 mL of distilled water, was added successively 8.6 mg (0.035 mmole) of Ni(OAc)$_2$.4H$_2$O and, at 0° C., 20 mL of an untitrated solution of dimethyldioxirane (0.05-0.10 M) in acetone. The resulting solution was allowed to warm to room temperature and stirred for 24 hours. The organic solvent was then evaporated in vacuo and the resulting aqueous residue was extracted with dichloromethane (four times). The organic extract was dried over Na$_2$SO$_4$ and concentrated in vacuo to afford 51 mg (0.317 mmol; 92% yield; >90% conversion) of ethyl 2-hydroxy-2-($^{13}$C)methyl-3-oxobutanoate as a colorless liquid which was pure enough to be used without further purification.

NMR spectroscopy: $^1$H NMR (CDCl$_3$); 4.25 (q, J=7.1 Hz, 2H), 2.27 (s, 3H), 1.58 (d, $^1J_{H-13C}$=130.3 Hz, 3H), 1.29 (t, J=7.1 Hz, 3H).

2-hydroxy-2-($^{13}$C)methyl-3-oxo-4-($^2$H$_3$)-butanoate (or 2-($^{13}$C)methyl-4-($^2$H$_3$)-acetolaetate) (Compound of Formula 4)

Deprotection and exchange of the protons of the methyl group in position 4 of ethyl 2-hydroxy-2-($^{13}$C)methyl-3-oxobutanoate (B) were achieved in D$_2$O at pH 13. Typically, 300 mg of B was added to 24 mL of a 0.1 M NaOD/D$_2$O solution. The deprotection was immediate as observed by NMR spectroscopy. The completion of the exchange on the 4-methyl was also followed in real time by NMR spectrometry. 97±1% of protons of terminal methyl groups have been exchanged after 30 min while the methyl subsistent in position 2 remains protonated at a level of 98±1%. As the deprotection reaction consumes hydroxide ions, the pH and consequently the deuterium exchange rate decreases during the reaction. Once the exchange was complete, the solution was adjusted to neutral pH with DCl and 2 mL of 1 M TRIS pH 8 in $D_2O$ was added. The solution of the compound of formula 4 was then stored at −20° C. until required.

Reaction Scheme of the Protocol for the Production of U—[$^2$H], U—[$^{15}$N], Leu/Val-[$^{13}$C$^1$H$_3$]$^{proS}$ Labeled Proteins.

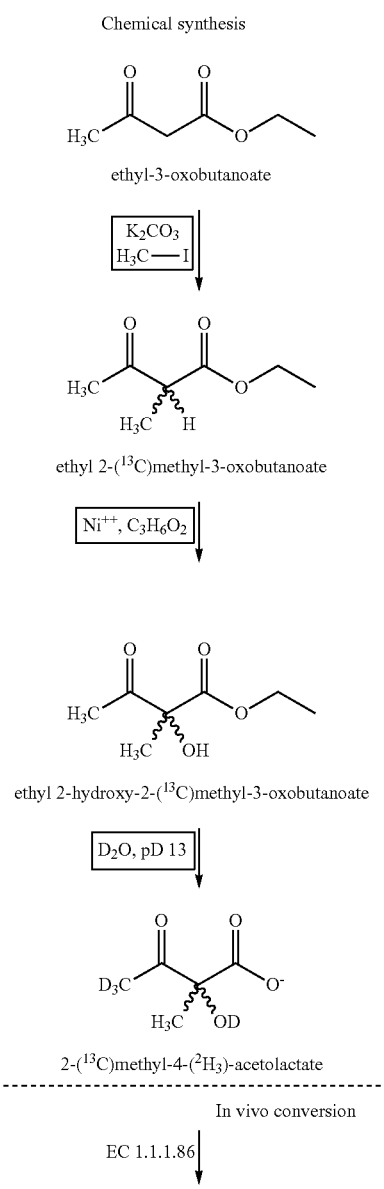

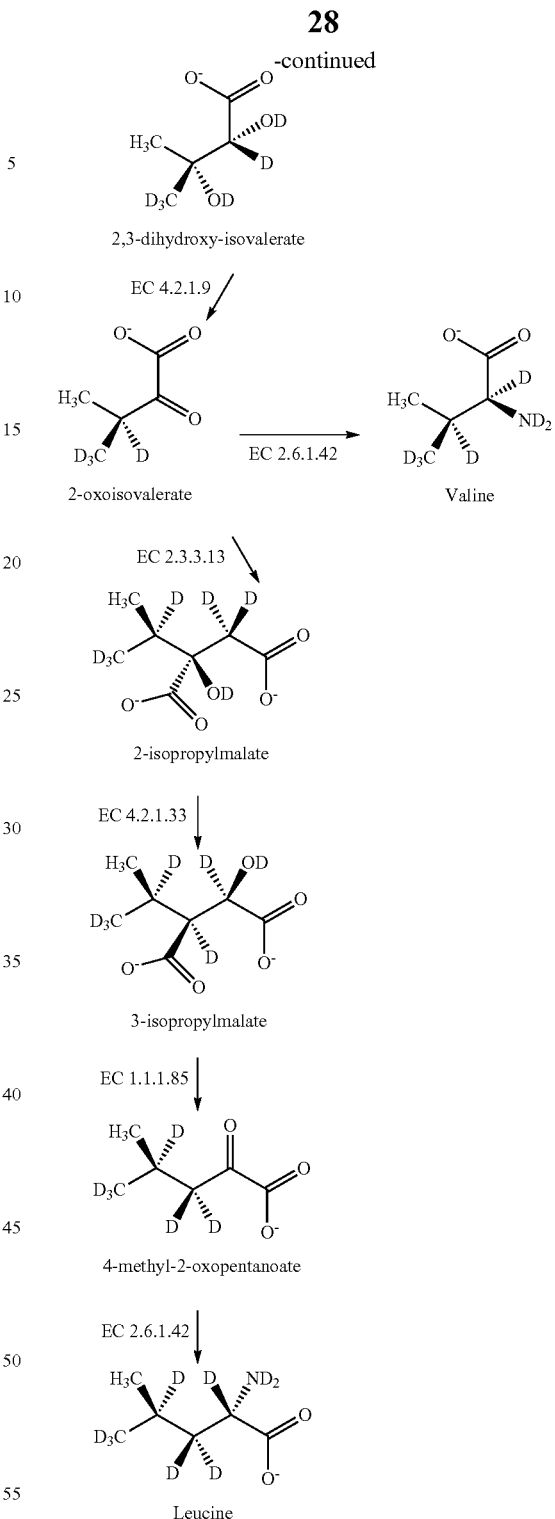

Detailed protocol for the chemical synthesis of 2-($^{13}$C) methyl-4-($^2$H$_3$)-acetolactate is presented above. $^{13}$C nuclei are displayed in italic bold. The stereochemistry, following the incorporation of $^{13}$C$^1$H$_3$ group into acetolactate, in the different intermediates of Leu/Val biogenesis pathway is indicated on the figure (assuming growth in M9/$D_2O$ based culture medium). Each biosynthetic intermediate has been named according to the Kyoto Encyclopedia of Genes and Genomes. The enzymes responsible for catalyzing reaction are indicated by EC number. EC 1.1.1.86: ketol-acid reductoisomerase; EC 4.2.1.9: dihydroxy-acid dehydratase; EC 2.6.1.42: branched-chain amino acid aminotransferase; EC 2.3.3.13: 2-isopropylmalate synthase; EC 4.2.1.33: 3-isopropylmalate dehydratase; EC 1.1.1.85: 3-isopropylmalate dehydrogenase. Further information on the Leu/Val metabolic pathway can be found online: http://www.genome.jp/kegg/.

2. Overexpression of Methyl Stereospecifically Labeled Proteins in *E. coli*

Optimization of the Incorporation of Acetolactate in Overexpressed Protein.

Initial experiments to determine the level of acetolactate incorporation into overexpressed proteins were performed using ubiquitin as a model system. *E. coli* BL21(DE3) cells were transformed with a pET41c plasmid carrying the human His-tagged ubiquitin (pET41c-His-Ubi) gene and transformants were grown in M9/$D_2O$ media containing 1 g/L $^{15}ND_4Cl$, and 2 g/L of U-[$^2H$], U-[$^{13}C$], glucose. When the optical density (O.D.) at 600 nm reached 0.8, a solution containing unlabeled acetolactate was added. After an additional 1 h, protein expression was induced by the addition of IPTG to a final concentration of 1 mM. Induction was performed for 3 hours at 37° C. Ubiquitin was purified by Ni-NTA (Qiagen) chromatography in a single step.

The optimal quantity of acetolactate required to achieve near complete incorporation in the overexpressed protein was assessed in a series of cultures (90 mL each) in which different amounts of unlabeled precursor were added 1 hour prior induction to final concentrations of 0, 100, 200, 300 and 800 mg/L. The level of incorporation into the purified protein was monitored by directly-detected $^{13}C$ 1D NMR. When the precursor is incorporated into the overexpressed protein, the $^{13}C$-L,V residues are replaced by amino acids with $^{12}C$ side chains. The quantification was performed by comparing the integral of signals of 4 isolated Leu/Val methyl resonances (19-21 ppm) with respect to the signals of the methyl groups of Ile, Ala (between 9-19 ppm). The addition of 300 mg of pure acetolactate per liter of M9/$D_2O$ culture medium achieves an incorporation level of 95% in Leu/Val side chains without detectable scrambling to other amino-acid biogenesis pathways Production of U—[$^2H$], U—[$^{15}N$], Leu/Val-[$^{13}C^1H_3$]$^{proS}$ Proteins.

*E. coli* BL21(DE3) carrying the plasmid of the overexpressed protein (TET2 or MSG) were progressively adapted, in three stages, over 24 h, to M9/$D_2O$ media containing 1 g/L $^{15}ND_4Cl$ and 2 g/L D-glucose-$d_7$ (Isotec). In the final culture, the bacteria were grown at 37° C. in M9 media prepared with 99.85% $D_2O$ (Eurisotop). When the O.D. (600 nm) reached 0.8, a solution containing 2-($^{13}C$)methyl-4-($^2H_3$)-acetolactate (compound of formula 4) (prepared with the protocol described above) was added. Acetolactate was added to the culture medium to a final concentration of 300 mg/L. 1 hour later, TET2 (/MSG) expression was induced by the addition of IPTG to a final concentration of 1 mM (/0.1 mM). Expression was performed for 3 hours (/12 hours) at 37° C. (/20° C.) before harvesting. For MSG, $^{13}C$ spectra were recorded at 37° C. in $D_2O$ on a NMR spectrometer operating at a proton frequency of 600 MHz. Only signals for Leu and Val methyl carbons were observed in $^{13}C$ spectra, indicating that $^{13}C^1H_3$ groups of acetolactate were not incorporated in metabolic pathway of other amino-acids.

Production of U—[$^2H$], U—[$^{15}N$], Ile-[$^{13}C^1H_3$]$^{\gamma 2}$ Proteins.

*E. coli* BL21(DE3) carrying the plasmid of the overexpressed protein (TET2 or MSG) were progressively adapted, in three stages, over 24 h, to M9/$D_2O$ media containing 1 g/L $^{15}ND_4Cl$ and 2 g/L D-glucose-$d_7$ (Isotec). In the final culture, the bacteria were grown at 37° C. in M9 media prepared with 99.85% $D_2O$ (Eurisotop). When the O.D. (600 nm) reached 0.8, a solution containing 2-($^2H_5$)ethyl-2-hydroxy-3-oxo-4($^{13}C$)butanoate (compound of formula 6) (prepared with the protocol described above) was added. Product was added to the culture medium to a final concentration of 300 mg/L. 1 hour later, TET2 (/MSG) expression was induced by the addition of IPTG to a final concentration of 1 mM (/0.1 mM). Expression was performed for 3 hours (/12 hours) at 37° C. (/20° C.) before harvesting.

Production of U—[$^2H$], U—[$^{15}N$], Leu/Val-[$^{13}C^1H_3$, $^{12}C^2H_3$] Proteins.

For aim of comparison, the production of perdeuterated proteins with non-stereospecific $^{13}C^1H$ labeling of Leu and Val methyl groups was achieved using the protocol used before the invention, i.e. the protocol described by V. Tugarinov et al., *J. Biomol. NMR* 2004, 28, 165-172 and R. Lichtenecker et al., *J. Am. Chem. Soc.* 2004, 126, 5348-5349.

This protocol is the protocol described above but with the addition 1 hour prior induction of 125 mg/L of 3-($^2H_3$)methyl-3-($^2H$)-4-($^{13}C$)-ketoisovalerate (Isotec) in place of 300 mg/L of labeled acetolactate (compound of formula 4).

Production of U—[$^2H$], U—[$^{15}N$], U—[$^{12}C$], U—[$^{13}C^1H_3$]$^{proS}$-Leu/Val, U—[$^{13}C^1H_3$]-Ala Proteins.

The production of perdeuterated proteins with stereospecific $^{13}C^1H$ labeling of Leu/Val proS methyl groups and Ala-positions was achieved using the general protocol described above but with the addition 1 hour prior induction of 800 mg/L of 2-(S)-2-($^2H$)-3-($^{13}C$)-Alanine (CortecNet) together with 300 mg/L of labeled acetolactate (compound of formula 4). A 2D $^{13}C$-methyl TROSY spectra was recorded at 37° C. in $D_2O$ on a NMR spectrometer operating at a proton frequency of 800 MHz. Only peaks corresponding to the expected signals of Alanine methyl groups and proS methyl groups of Leu and Val side chains were observed indicating that labeling using acetolactate derivatives does not interference with other methyl labeling processes.

Proteins Purification.

Malate Synthase G (MSG) was purified initially by Chelating Sepharose chromatography (GE Healthcare) followed by gel filtration chromatography (Superdex 200 pg GE Healthcare). Typical final yields after purification were 60-80 mg/L of methyl specific protonated MSG. The concentration of MSG in typical NMR samples was 1 mM in 100% $D_2O$ buffer containing 25 mM MES (pH 7.0 uncorrected), 20 mM $MgCl_2$, 5 mM DTT. NMR data were acquired at 37° C.

TET2 was purified using two anion exchange chromatography steps (DEAE Sepharose CL-6B, and Resource Q 6 mL, GE Healthcare) followed by gel filtration (Sephacryl S-300 HR, GE Healthcare). Typical final yield after purification was 20 mg/L of methyl specific protonated TET2. Samples prepared in this manner were demonstrated to be fully active (measured by hydrolytic activity using Leu-4-nitroanitide). The final NMR samples of TET consisted of ~80 μM TET2 dodecamer (~1 mM monomer) in 20 mM Tris (pH 7.4 uncorrected), 20 mM NaCl dissolved in 300 μL $D_2O$. NMR data were acquired at 50° C.

3. NMR Spectroscopy

Experimental Details

All $^1H$ and $^{13}C$ 1D NMR spectra of ubiquitin and MSG were recorded on a Varian DirectDrive spectrometer operating at a proton frequency of 600 MHz equipped with a cryogenic triple resonance pulsed field gradient probehead.

2D methyl-TROSY spectra were recorded on a Varian DirectDrive spectrometer operating at a proton frequency of 800 MHz equipped with a cryogenic triple resonance pulsed field gradient probehead. The $^1$H-$^{13}$C HMQC of MSG (/TET2) were recorded with 1288 (/780) complex data points in direct dimension (maximum $t_2$=99 ms (/60 ms)) and 512 (/380) points in carbon dimension (maximum $t_1$=128 ms (/47 ms)).

The 4D HMQC-NOESY-HMQC experiments were recorded on a Varian DirectDrive spectrometer operating at a proton frequency of 800 MHz equipped with a cryogenic triple resonance pulsed field gradient probehead. Data were acquired in 96 h of a 1 mM sample of MSG with a NOE mixing time of 300 ms. The experiments were collected with 20 complex points in the indirect $^1$H dimension (maximum $t_1$=30 ms), 36 and 18 complex points in the first and second carbon dimension (maximum $t_2$=21 ms & $t_3$=11 ms), and 201 complex points in the direct dimension (maximum $t_4$=80 ms) and 4 scans per increment. All data were processed and analyzed using nmrPipe/nmrDraw and NMR-View. Distances were quantified using a full relaxation matrix analysis of NOEs between remote protons in methyl-specific protonated proteins as described in Sounier et al., *J. Am. Chem. Soc.* 2007, 129, 472-473.

Comparison of Methyl-TROSY Spectra Recorded on Leu/Val Methyl-Specifically Labeled TET2 Samples (468 kDa).

2D $^{13}$C-methyl TROSY spectra were recorded at 50° C. in D$_2$O on a NMR spectrometer operating at a proton frequency of 800 MHz for U—[$^2$H], U—[$^{12}$C], Leu/Val-[$^{12}$C$^2$H$_3$, $^{13}$C$^1$CH$_3$] TET2 with non-stereospecific [$^{13}$C$^1$H$_3$]-methyl labeling prepared using 3-($^2$H$_3$)methyl-3-($^2$H)-4-($^{13}$C)-ketoisovalerate; and for U—[$^2$H], U—[$^{12}$C], Leu/Val-[$^{13}$C$^1$H$_3$]$^{proS}$ TET2 with stereospecific labeling prepared using 2-($^{13}$C)methyl-4-($^2$H$_3$)-acetolactate (compound of formula 4). Preparation of TET2 assembly using a non-stereoselectively labeling scheme results in spectra with substantial cross-peak overlap that would have greatly hampered the observation of amastatin-induced chemical shift changes (Amastatin is an inhibitor of TET2).

The invention claimed is:

1. A process for the specific isotopic labeling of an amino acid selected from Valine (Val), Leucine (Leu), and Isoleucine (Ile), in proteins and biomolecular assemblies comprising:
   a) introducing, in a medium containing bacteria overexpressing a protein, a composition consisting essentially of an acetolactate derivative of Formula I:

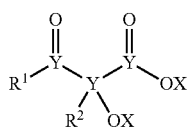

Formula I wherein:
   X is $^1$H or $^2$H (D),
   each Y is independently from the others $^{12}$C or $^{13}$C,
   R$^1$ is a methyl group in which the carbon atom is $^{13}$C or $^{12}$C and the hydrogen atoms are independently from each other $^1$H or $^2$H (D),
   R$^2$ is either a methyl group in which the carbon atom is $^{13}$C or $^{12}$C and the hydrogen atoms are independently from each other $^1$H or $^2$H (D), or an ethyl group in which the carbon atoms are independently from each other $^{13}$C or $^{12}$C and the hydrogen atoms are independently from each other $^1$H or $^2$H (D),
with the proviso that:
   the hydrogen atoms of R$^1$ and the hydrogen atoms of R$^2$ are not all, at the same time, either $^1$H or $^2$H (D).

2. The process of claim 1 further comprising:
   b) overexpression of the protein by the bacteria contained in the medium, and
   c) purification of the protein.

3. The process of claim 1, wherein in the acetolactate derivative of Formula I:
   R$^1$ is chosen from the following groups:
   $^{12}$CH$_3$, $^{12}$CD$_3$, $^{13}$CH$_3$, $^{13}$CD$_3$, $^{13}$CHD$_2$, $^{13}$CH$_2$D, and
   R$^2$ is chosen from the following groups:
   $^{12}$CH$_3$, $^{12}$CD$_3$, $^{13}$CH$_3$, $^{13}$CD$_3$, $^{13}$CHD$_2$, $^{13}$CH$_2$D, $^{12}$CH$_3$$^{12}$CD$_2$, $^{12}$CD$_3$$^{12}$CD$_2$, $^{13}$CH$_3$$^{12}$CD$_2$, $^{13}$CH$_3$$^{13}$CD$_2$, $^{13}$CD$_3$$^{13}$CD$_2$, $^{13}$CHD$_2$$^{13}$CD$_2$, $^{13}$CH$_2$D$^{13}$CD$_2$, $^{13}$CHD$_2$$^{12}$CD$_2$, $^{13}$CH$_2$D$^{12}$CD$_2$.

4. The process of claim 1, wherein the acetolactate derivative of Formula I is selected from the following compounds:
   2-hydroxy-2-($^{13}$C)methyl-3-oxo-4-($^2$H$_3$)butanoic acid,
   2-hydroxy-2-($^2$H$_3$)methyl-3-oxo-4-($^{13}$C)butanoic acid,
   2-($^2$H$_5$)ethyl-2-hydroxy-3-oxo-4-($^{13}$C)methylbutanoic acid,
   1,2,3,4-($^{13}$C)-2-($^2$H$_5$)ethyl-2-hydroxy-3-oxobutanoic acid,
   1,2,3-($^{13}$C)-2-($^{13}$C)methyl-2-hydroxy-3-oxo-4-($^2$H$_3$)butanoic acid,
   1,2,3,4-($^{13}$C)-2-($^2$H$_3$)methyl-2-hydroxy-3-oxobutanoic acid,
   1,2,3-($^{13}$C)-2-(1'-($^2$H$_2$), $^{13}$C$_2$)ethyl)-2-hydroxy-3-oxo-4-($^2$H$_3$)butanoic acid,
   3,4-($^{13}$C)-2-($^{13}$C)methyl-2-hydroxy-3-oxo-4-($^2$H$_3$)butanoic acid,
   3,4-($^{13}$C)-2-($^2$H$_3$, $^{13}$C)methyl-2-hydroxy-3-oxobutanoic acid,
   3,4-($^{13}$C)-2-(1'-($^2$H$_2$), $^{13}$C$_2$)ethyl-2-hydroxy-3-oxo-4-($^2$H$_3$)butanoic acid,
   3,4-($^{13}$C)-2-($^2$H$_5$, $^{13}$C$_2$)ethyl-2-hydroxy-3-oxobutanoic acid, and
   3,4-($^{13}$C)-2-(1'-($^2$H$_2$),$^{13}$C$_2$)ethyl-2-hydroxy-3-oxobutanoic acid.

5. The process of claim 1, wherein the acetolactate derivative of Formula I is selected from the following compounds:
   2-hydroxy-2-($^2$H$_2$, $^{13}$C)methyl-3-oxo-4-($^2$H$_3$)butanoic acid,
   2-hydroxy-2-($^2$H$_3$)methyl-3-oxo-4-($^2$H$_2$, $^{13}$C)butanoic acid,
   2-($^2$H$_5$)ethyl-2-hydroxy-3-oxo-4-($^2$H$_2$, $^{13}$C)butanoic acid, and
   2-(1'-($^2$H$_2$),2'-($^2$H),2'-($^{13}$C))ethyl-2-hydroxy-3-oxo-4-($^2$H$_3$)butanoic acid.

6. The process of claim 1, wherein the acetolactate derivative of Formula I is selected from the following compounds:
   2-hydroxy-2-($^2$H, $^{13}$C)methyl-3-oxo-4-($^2$H$_3$)butanoic acid,
   2-hydroxy-2-($^2$H$_3$)methyl-3-oxo-4-($^2$H, $^{13}$C)butanoic acid, and
   2-($^2$H$_5$)ethyl-2-hydroxy-3-oxo-4-($^2$H, $^{13}$C)butanoic acid.

7. The process of claim 1, wherein said process specifically isotopically labels Valine in proteins and biomolecular assemblies.

8. The process of claim 1, wherein said process specifically isotopically labels Leucine in proteins and biomolecular assemblies.

9. The process of claim 1, wherein said process specifically isotopically labels Isoleucine in proteins and biomolecular assemblies.

10. The process of claim 1, wherein said process specifically isotopically labels methyl groups of Leucine and Valine in proteins and biomolecular assemblies.

11. The process of claim 1, wherein said process specifically isotopically labels γ2-methyl groups of Isoleucine in proteins and biomolecular assemblies.

12. A process for analyzing a protein by NMR, comprising labeling a protein to be analyzed by the process of claim 1.

* * * * *